(12) United States Patent
McDonald

(10) Patent No.: US 8,118,166 B2
(45) Date of Patent: Feb. 21, 2012

(54) PACKAGING WITH EASY OPEN FEATURE

(75) Inventor: Duane L. McDonald, Neenah, WI (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 1871 days.

(21) Appl. No.: 10/749,988

(22) Filed: Dec. 31, 2003

(65) Prior Publication Data

US 2004/0168947 A1 Sep. 2, 2004

Related U.S. Application Data

(63) Continuation-in-part of application No. 10/366,872, filed on Feb. 14, 2003.

(51) Int. Cl.
*B65D 73/00* (2006.01)

(52) U.S. Cl. .................... 206/494; 206/440

(58) Field of Classification Search ............ 206/438, 206/440, 441, 494, 459.1, 460–463, 466, 206/467, 470; 604/385.01, 385.02, 385.19
See application file for complete search history.

(56) References Cited

U.S. PATENT DOCUMENTS

| | | |
|---|---|---|
| 1,994,135 A | 3/1935 | Horowitz |
| 2,145,137 A | 1/1939 | Sayers |
| 2,676,702 A * | 4/1954 | Whitefoot, Jr ............. 206/440 |
| 2,764,859 A | 10/1956 | Hanselmann |
| 2,845,069 A | 7/1958 | Jamison et al. |
| 2,935,828 A | 5/1960 | Mahaffy et al. |
| 3,286,435 A * | 11/1966 | Weinberger ................ 53/117 |
| 3,343,336 A | 9/1967 | Bradford |
| 3,403,776 A * | 10/1968 | Denny ...................... 206/363 |
| 3,442,686 A | 5/1969 | Jones |
| 3,561,446 A | 2/1971 | Jones, Sr. |
| 3,605,746 A | 9/1971 | Schaar |
| 3,645,060 A | 2/1972 | Hammond |
| 3,652,006 A * | 3/1972 | Trewella ................... 206/440 |
| 3,673,757 A * | 7/1972 | Willis ....................... 53/429 |
| 3,710,797 A | 1/1973 | Marsan |
| 3,747,601 A | 7/1973 | May, Jr. |
| 3,794,033 A | 2/1974 | Ryan |
| 3,824,759 A | 7/1974 | Finn et al. |
| 3,938,523 A | 2/1976 | Gilliland et al. |
| 3,938,659 A * | 2/1976 | Wardwell .................. 206/440 |
| 3,963,029 A | 6/1976 | Brooks |
| 3,970,217 A | 7/1976 | Culbertson et al. |
| 4,034,760 A | 7/1977 | Amirsakis |
| 4,050,462 A | 9/1977 | Woon et al. |
| 4,076,663 A | 2/1978 | Masuda et al. |
| 4,242,854 A | 1/1981 | Nissen |

(Continued)

FOREIGN PATENT DOCUMENTS

CH 671145 8/1989

(Continued)

OTHER PUBLICATIONS

Derwent World Patent Database abstract of IL 67419: Description of Porat et al., "Bandage Made of Absorbent Material."

(Continued)

*Primary Examiner* — Luan K Bui

(74) *Attorney, Agent, or Firm* — Randall W. Fieldhack

(57) ABSTRACT

A package enclosing a single disposable absorbent article. The package having an opening element.

22 Claims, 14 Drawing Sheets

U.S. PATENT DOCUMENTS

| | | | |
|---|---|---|---|
| 4,264,008 A * | 4/1981 | Kozlow | 206/441 |
| 4,265,070 A | 5/1981 | Mainberger et al. | |
| 4,286,082 A | 8/1981 | Tsubakimoto et al. | |
| 4,556,146 A | 12/1985 | Swanson et al. | |
| 4,573,608 A | 3/1986 | Hansen | |
| 4,576,596 A | 3/1986 | Jackson et al. | |
| 4,585,448 A | 4/1986 | Enloe | |
| 4,597,494 A * | 7/1986 | Benoit | 206/494 |
| 4,598,528 A | 7/1986 | McFarland et al. | |
| 4,630,320 A | 12/1986 | Van Gompel | |
| 4,641,381 A | 2/1987 | Heran et al. | |
| 4,646,362 A | 3/1987 | Heran et al. | |
| 4,696,393 A * | 9/1987 | Laipply | 206/441 |
| 4,702,378 A | 10/1987 | Finkel et al. | |
| 4,704,116 A | 11/1987 | Enloe | |
| 4,765,477 A | 8/1988 | Froidh et al. | |
| 4,798,603 A | 1/1989 | Meyer et al. | |
| 4,801,005 A * | 1/1989 | Hahn et al. | 206/494 |
| 4,802,884 A | 2/1989 | Froidh et al. | |
| 4,833,862 A | 5/1989 | Bortolani et al. | |
| 4,886,512 A | 12/1989 | Damico et al. | |
| 4,896,768 A * | 1/1990 | Anderson | 206/210 |
| 4,917,675 A * | 4/1990 | Taylor et al. | 206/440 |
| 4,934,535 A | 6/1990 | Muckenfuhs et al. | |
| 5,016,778 A | 5/1991 | Reiland et al. | |
| 5,040,677 A * | 8/1991 | Tubo et al. | 206/440 |
| 5,065,868 A | 11/1991 | Cornelissen et al. | |
| 5,141,505 A | 8/1992 | Barrett | |
| 5,176,668 A | 1/1993 | Bernardin | |
| 5,192,606 A | 3/1993 | Proxmire et al. | |
| 5,255,817 A | 10/1993 | Reiland et al. | |
| 5,295,988 A | 3/1994 | Muckenfuhs et al. | |
| 5,304,158 A | 4/1994 | Webb | |
| 5,333,753 A * | 8/1994 | Etheredge | 206/441 |
| 5,383,872 A | 1/1995 | Roessler et al. | |
| 5,413,568 A | 5/1995 | Roach et al. | |
| 5,457,895 A * | 10/1995 | Thompson et al. | 34/296 |
| 5,462,166 A | 10/1995 | Minton et al. | |
| 5,484,636 A | 1/1996 | Berg, Jr. et al. | |
| 5,509,915 A | 4/1996 | Hanson et al. | |
| 5,520,674 A | 5/1996 | Lavon et al. | |
| 5,564,261 A | 10/1996 | Kiner | |
| 5,651,778 A | 7/1997 | Melius et al. | |
| 5,666,787 A | 9/1997 | Young et al. | |
| 5,766,389 A | 6/1998 | Brandon et al. | |
| 5,897,542 A | 4/1999 | Lash et al. | |
| 5,950,830 A * | 9/1999 | Trigger | 206/440 |
| 5,964,351 A | 10/1999 | Zander | |
| 5,971,153 A | 10/1999 | Bauer et al. | |
| 6,004,307 A | 12/1999 | Colon et al. | |
| 6,028,240 A | 2/2000 | Wessel et al. | |
| 6,040,494 A | 3/2000 | Kalentun et al. | |
| 6,050,984 A | 4/2000 | Fujioka et al. | |
| 6,079,562 A | 6/2000 | Bauer et al. | |
| 6,131,736 A * | 10/2000 | Farris et al. | 206/440 |
| 6,260,211 B1 | 7/2001 | Rajala et al. | |
| 6,264,972 B1 | 7/2001 | Drury | |
| 6,297,424 B1 | 10/2001 | Olson et al. | |
| 6,316,687 B1 | 11/2001 | Davis et al. | |
| 6,321,513 B1 | 11/2001 | Meixner | |
| 6,387,085 B1 | 5/2002 | Van Gompel et al. | |
| 6,443,938 B1 | 9/2002 | Vogt | |
| 6,458,110 B1 | 10/2002 | Lavon et al. | |
| 6,475,199 B1 | 11/2002 | Gann et al. | |
| 6,497,692 B1 | 12/2002 | Tameishi et al. | |
| 6,500,160 B2 | 12/2002 | Mizutani et al. | |
| 6,502,695 B1 | 1/2003 | Kim et al. | |
| 6,575,947 B1 | 6/2003 | Tameishi et al. | |
| 6,630,237 B2 | 10/2003 | Rivett et al. | |
| 6,640,976 B1 * | 11/2003 | Franks-Farah et al. | 206/440 |
| 2002/0078665 A1 | 6/2002 | Salman et al. | |
| 2002/0079246 A1 | 6/2002 | Ling et al. | |
| 2002/0125171 A1 | 9/2002 | Kuske et al. | |
| 2002/0170275 A1 | 11/2002 | Salman et al. | |
| 2003/0065300 A1 | 4/2003 | Suga | |
| 2003/0065302 A1 | 4/2003 | Kuroda et al. | |
| 2003/0073970 A1 | 4/2003 | Suga | |
| 2004/0167489 A1 | 8/2004 | Kellenberger et al. | |
| 2004/0167490 A1 | 8/2004 | Nelson et al. | |
| 2004/0172002 A1 | 9/2004 | Nelson et al. | |
| 2004/0173490 A1 | 9/2004 | Otsubo | |
| 2004/0176735 A1 | 9/2004 | Snell | |

FOREIGN PATENT DOCUMENTS

| | | |
|---|---|---|
| DE | 29620118 U1 | 4/1998 |
| EP | 0 747 295 A1 | 12/1996 |
| EP | 0 539 703 B1 | 3/1997 |
| EP | 0 938 437 B1 | 1/2001 |
| EP | 1 174 104 A1 | 1/2002 |
| EP | 1 205 171 A2 | 5/2002 |
| EP | 1 413 272 A1 | 4/2004 |
| GB | 2 277 914 A | 11/1994 |
| JP | 10-095481 * | 4/1998 |
| JP | 10-095481 A | 4/1998 |
| JP | 10-305059 A | 11/1998 |
| JP | 11-113956 A | 4/1999 |
| JP | 2000-043818 A | 2/2000 |
| JP | 2001-114214 A | 4/2001 |
| JP | 2002-337814 A | 11/2002 |
| WO | WO 89/00037 A1 | 1/1989 |
| WO | WO 90/01311 A1 | 2/1990 |
| WO | WO 95/32698 A1 | 12/1995 |
| WO | WO 96/41753 A1 | 12/1996 |
| WO | WO 97/33815 A1 | 9/1997 |
| WO | WO 98/57675 A1 | 12/1998 |
| WO | WO 99/03436 A1 | 1/1999 |
| WO | WO 00/19953 A1 | 4/2000 |
| WO | WO 00/19954 A1 | 4/2000 |
| WO | WO 02/085271 A1 | 10/2002 |
| WO | WO 02/094678 A1 | 11/2002 |
| WO | WO 02/096331 A2 | 12/2002 |
| WO | WO 2005/005276 A1 | 1/2005 |

OTHER PUBLICATIONS

Derwent World Patent Database abstract of JP 3169863 BS: Description of Shiseido Co Ltd., "Individual Packaging Method of Sanitary Product."

Derwent World Patent Database abstract of JP 3400659 B2: Description of Kawshiwagi et al., "Bagged Sanitary Towel."

Derwent World Patent Database abstract of JP 3403120 B2: Description of KOA Corp, "Packing Unit for Absorption Goods."

TAPPI Official Test Method T 543 pm-84, "Stiffness of Paper," published by the TAPPI Press, Atlanta, Georgia, revised 1984, pp. 1-3.

Ida P., "Just for Baby." Quick Tips, FoodSaver, America's #1 Selling Brand of Home Vacuum Packaging Systems, Jun. 15, 2004, accessed Sep. 15, 2005, at Internet wep page "www.foodsaver.com/quicktips.ad2", 9 pages.

* cited by examiner

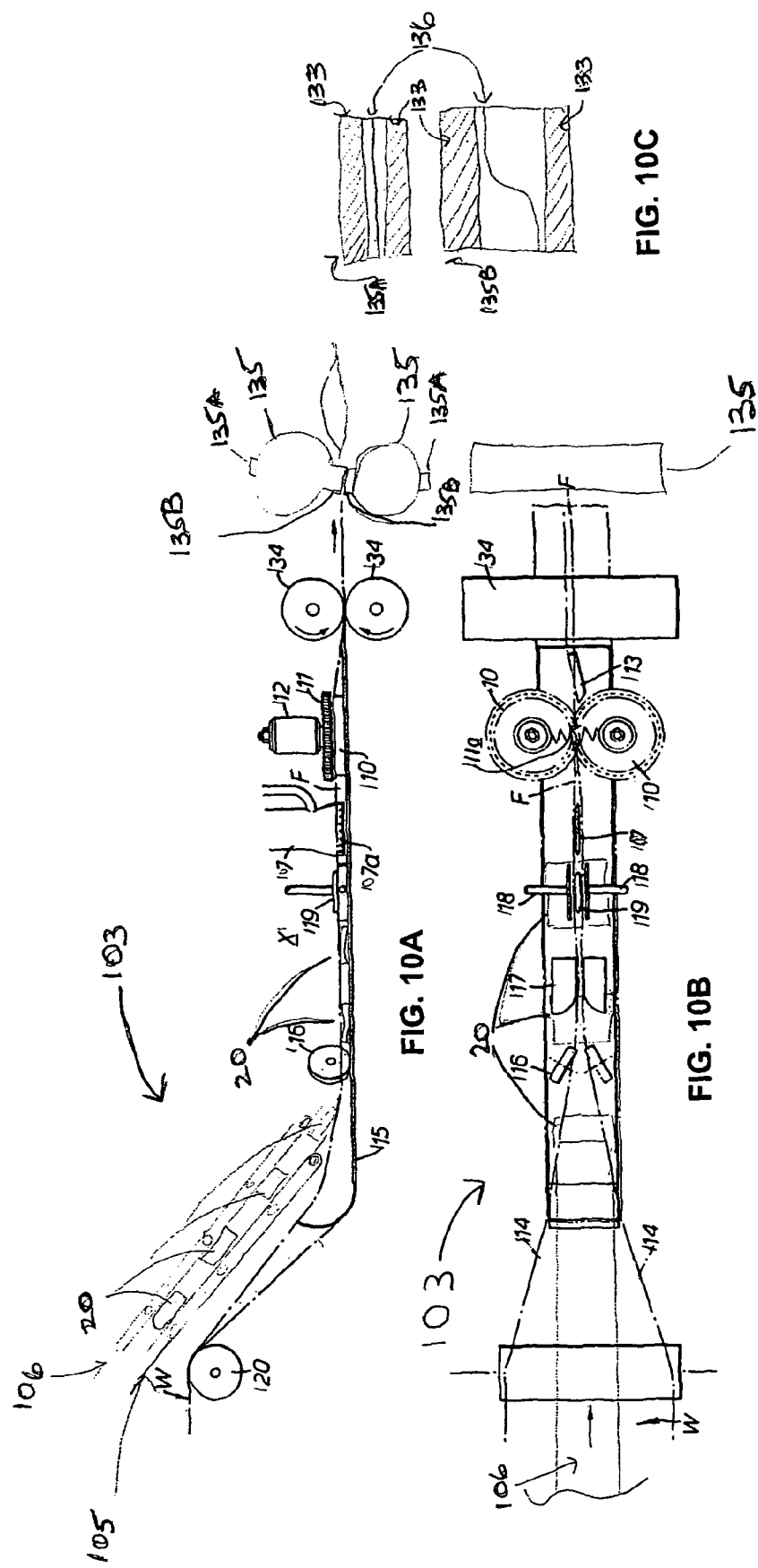

FIG. 12A　　FIG. 13A　　FIG. 14A
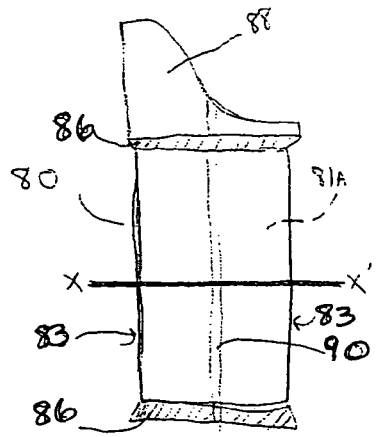
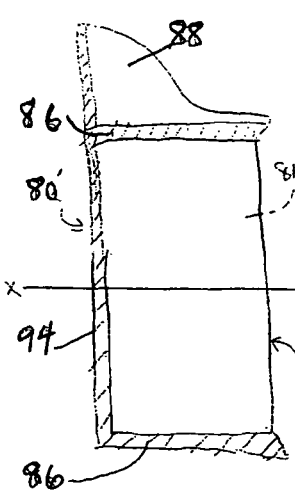
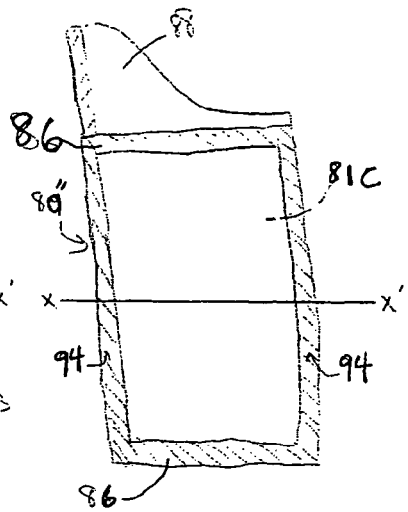
FIG. 12B　　FIG. 13B　　FIG. 14B
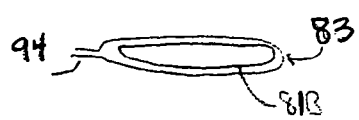
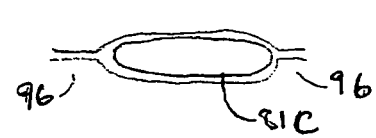
FIG. 12C
FIG. 15
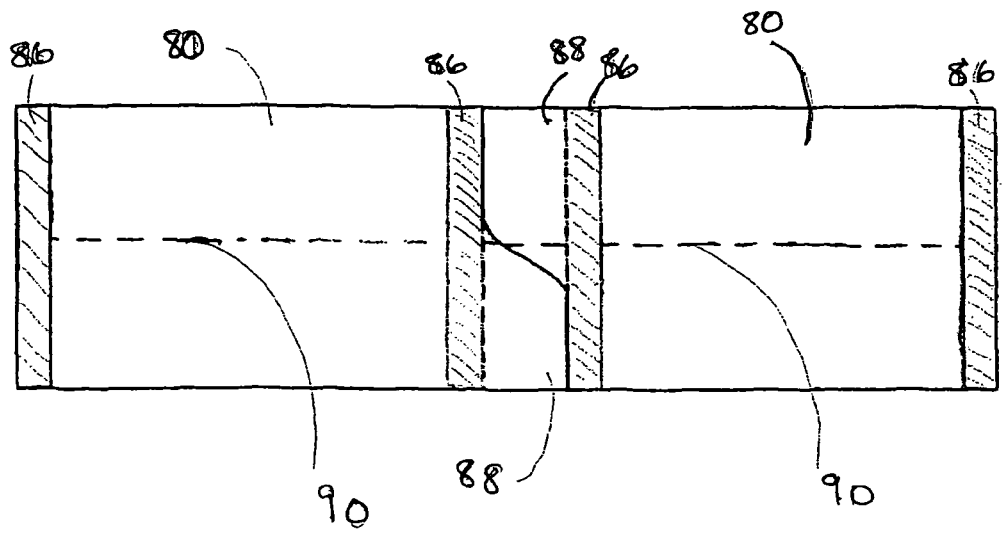

PACKAGING WITH EASY OPEN FEATURE

REFERENCE TO PRIOR APPLICATION

This is a continuation-in-part of U.S. patent application Ser. No. 10/366,872, filed Feb. 14, 2003, pending hereby incorporated herein by reference.

BACKGROUND

The present invention relates to packaging for disposable absorbent articles. More particularly, the present invention relates to packaging containing a single disposable absorbent article, the packaging having an easy open feature.

Disposable absorbent articles such as, for example, diapers, training pants and incontinence garments desirably provide a comfortable fit about the wearer and contain body exudates. Such disposable absorbent articles are commercially packaged in packages which include multiple disposable absorbent articles therein.

Conventional packages containing multiple disposable absorbent articles have either contained no opening feature, or in some commercial packages a portion of the package may have been perforated forming a weakness which aided the user in opening the package. Because these packages contain multiple disposable absorbent articles, are typically opened in the home, and are only opened once per multiple articles, many of the opening features provided have been adequate. Additionally, these packages are large in comparison to user's hands and fingers, allowing the user to easily obtain a grip on the package thus providing the user with a mechanism to easily open the package and retrieve the products inside.

Space, modesty, and portability considerations, however, illustrate that a need exists for a package containing a single disposable absorbent article. Further, these considerations also illustrate that a need exists for a package containing a single disposable absorbent article, which is provided in a much smaller, folded configuration compared to its expanded in-use, unfolded configuration. Such a packaged disposable absorbent article would desirably be sized to fit into a purse or a standard shirt or pants pocket.

Packages containing a single disposable absorbent article, however present unique challenges with regard to opening. First, the packages contain a single disposable absorbent article and are relatively small compared to the user's hands and fingers making it difficult for the user to grasp a portion of the package for opening. Second, discreetness and portability concerns may lead to the single disposable absorbent article being packaged very tightly, again causing difficulty in opening. Third, a single disposable absorbent article may be vacuumed packaged requiring tougher, "air tight" materials which may be difficult to tear open. These factors result in packages containing a single disposable absorbent article being more difficult to open than packages containing multiple disposable absorbent articles. Furthermore, since a package containing a single disposable absorbent article must be opened every time a disposable absorbent article is used, any difficulty in opening the package is experienced every time a disposable absorbent article is used. Consequently, there has remained a need to provide packages containing a single disposable absorbent article that are easy to open.

SUMMARY

In response to the foregoing need, the present inventor undertook intensive research and development efforts that resulted in the discovery of a package for enclosing a single disposable absorbent article. One version of the package of the present invention includes a first piece of material and a second piece of material. The first piece of material and the second piece of material are operatively associated with one another to enclose the absorbent article. The operative association defines a seal. Additionally, at least a portion of the first piece of material and at least a portion of the second piece of material extend beyond the seal to deliver an opening element.

Another version of the present invention provides a package enclosing a single disposable absorbent article. The package includes a layer of material having an interior surface and an exterior surface. The layer of material is configured to provide an interior space and at least two lateral seals. The absorbent article is situated within the interior space of the package. A portion of the layer of material extends beyond at least one lateral seal to provide an opening element.

Still another version of the present invention discloses yet another package enclosing a single disposable absorbent article. The package includes a first piece of material and a second piece of material. The first piece of material and the second piece of material are operatively associated with one another to enclose the absorbent article. The operative association defines a seal. The seal defines at least one lateral edge and at least one longitudinal edge. At least a portion of the first piece of material and at least a portion of the second piece of material extend beyond the seal to deliver an opening tab. Additionally, a portion of the opening tab extends beyond at least one lateral edge of the seal, and a portion of the opening tab extends beyond at least one longitudinal edge of the seal.

DRAWINGS

The foregoing and other features, aspects and advantages of the present invention will become better understood with regard to the following description, appended claims and accompanying drawings, where:

FIG. 10A illustrates an elevation view of an alternative apparatus for packaging disposable absorbent articles;

FIG. 10B illustrates a plan view of the apparatus of FIG. 10A;

FIG. 10C illustrates a perspective view of the sealing region from FIG. 10A;

FIGS. 12A-12C illustrate a version of an alternative package in which disposable absorbent articles may be packaged;

FIGS. 13A-13B illustrate a version of an alternative package in which disposable absorbent articles may be packaged;

FIGS. 14A-14B illustrate a version of a further alternative package in which disposable absorbent articles may be packaged;

FIG. 15 illustrates two packages with nested opening elements placed adjacent to one another;

DESCRIPTION

Figure 1:
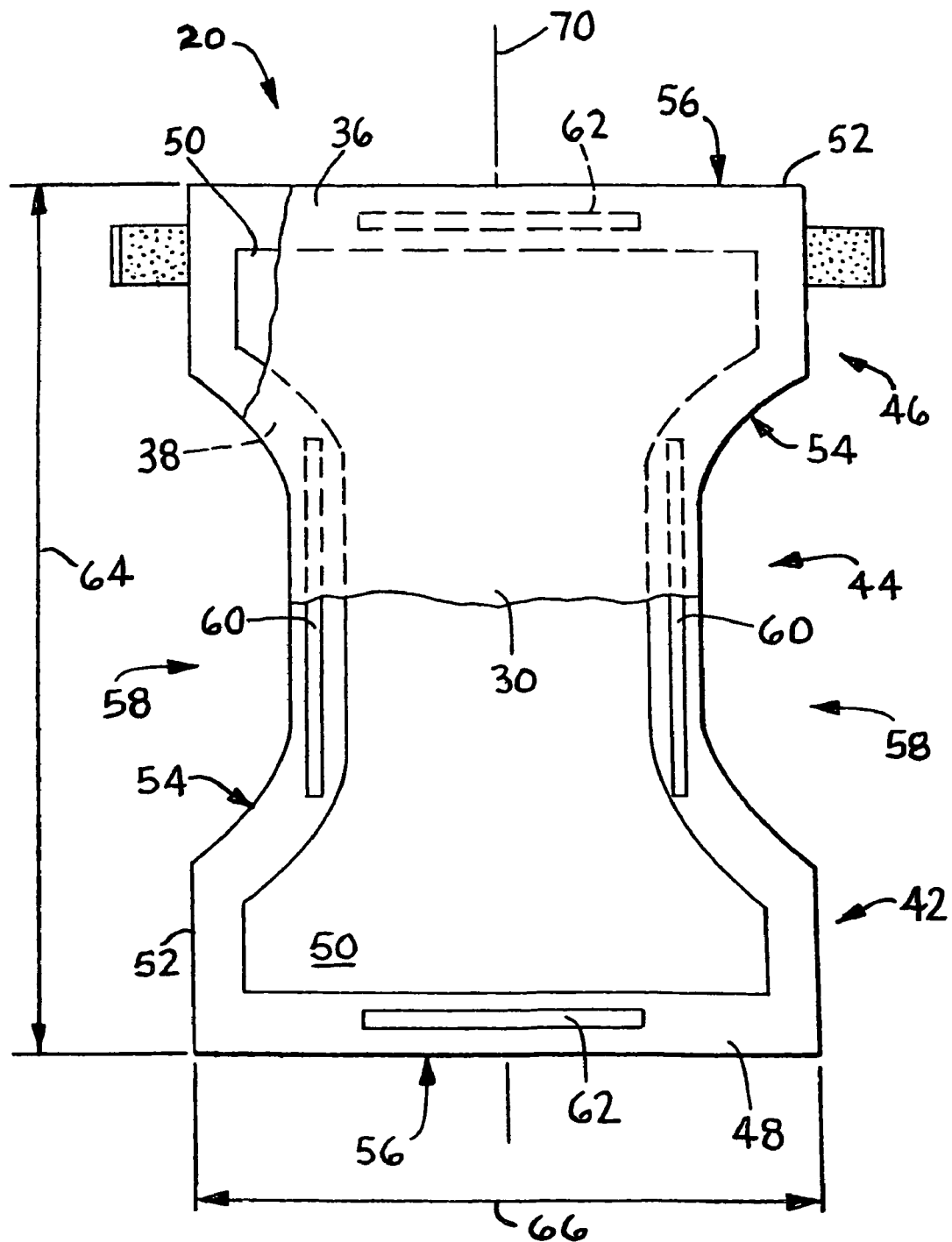
FIG. 1 illustrates a plan view of a disposable absorbent article in an unfastened, stretched and laid flat condition with the surface of the article which contacts the wearer's skin facing the viewer and with portions of the article partially cut away to show the underlying features.

The present disclosure of the invention will be expressed in terms of its various components, elements, constructions, configurations, arrangements and other features that may also be individually or collectively referenced by the term, "aspect(s)" of the invention, or other similar terms. It is contemplated that the various forms of the disclosed invention may incorporate one or more of its various features and aspects, and that such features and aspects may be employed in any desired, operative combination thereof.

It has been discovered that disposable absorbent articles, such as a diaper, a training pant, or an adult incontinence pant or garment, may be packaged individually in a package with a feature to provide for easy opening. Such a packaging provides the end-user with a portable, convenient, and discrete method for using disposable absorbent products. Absorbent articles may be packaged individually in packages including one, two, or more pieces of packaging material. These packages may contain an absorbent article that is in an unfolded configuration or the article may be folded one or more times to provide a smaller more discreet package.

Versions of the packages of the present invention desirably present the user with an opening element that provides the user with a location to grasp the package facilitating opening. This opening element may be provided on a package formed from one, two, or more individual pieces of material. Desirably this opening element provides the user with a method to open the package at a seal with a controlled opening. This controlled opening, allows the user to create an opening in the package for removal of the disposable absorbent article, without separating the package into two unconnected pieces.

The packages of the present invention may be formed in a number of different ways. The package may be formed in a batch process where a single package is formed at a time. Alternatively, the package may be formed in a batch process where multiple packages are formed at a time, and alternatively, the package may be formed in a continuous process where a number of packages are formed in uninterrupted succession. Further, the packages of the present invention may be formed in a combination of methods, such as, by way of non-limiting example, the absorbent articles being folded in a continuous process, and then packaged in either a single package batch process or multiple package batch process.

Reference will now be made in detail to one or more versions of the invention, examples of which are illustrated in the drawings. Each example and version is provided by way of explanation of the invention, and not meant as a limitation of the invention. For example, features illustrated or described as part of one version may be used with another version to yield still a further version. It is intended that the invention include these and other modifications and variations as coming within the scope and spirit of the invention.

The present invention is directed toward packages containing a single disposable absorbent article which may be used to absorb body exudates, and which is designed to cover at least a portion of a lower torso when worn by a wearer. It will be appreciated, however, that descriptions, figures, examples, test(s), and so forth of a particular packaged disposable article, such as a diaper, are only by way of example, and are intended as non-limiting in the scope and spirit of the invention.

The disposable absorbent articles may include other types of absorbent articles, such as adult incontinent products, training pants, other personal care or health care garments, diaper pants and other types of garment-style disposable absorbent articles. Diapers are disclosed in U.S. Pat. No. 4,704,116 to Enloe, U.S. Pat. No. 4,050,462 to Woon et al., U.S. Pat. No. 5,383,872 to Roessler et al., U.S. Pat. No. 6,028,240 to Wessel et al., U.S. Pat. No. 6,316,687 to Davis et al., and U.S. Pat. No. 6,443,938 to Vogt. Training pants are disclosed in U.S. Pat. No. 4,641,381 to Heran et al., U.S. Pat. No. 4,646,362 to Heran et al., U.S. Pat. No. 5,766,389 to Brandon et al., and U.S. Pat. No. 6,297,424 to Olson et al. Adult incontinence products are disclosed in U.S. Pat. No. 4,630,320 to Van Gompel, U.S. Pat. No. 4,886,512 to Damico et al., U.S. Pat. No. 5,651,778 to Melius et al., U.S. Pat. No. 6,260,211 to Rajala et al., and U.S. Pat. No. 6,387,085 to Van Gompel et al.

Turning now to the drawings, FIG. 1 illustrates a disposable diaper 20 as having a front portion 42, a rear portion 46, and a crotch portion 44 located between the front and rear portions. The disposable diaper includes an outer cover 48, a bodyside liner 30, and an absorbent structure 50 situated between the outer cover 48 and the liner 30. The outer edges of the diaper 20 define a periphery 52 with laterally opposed, longitudinally extending side edges 54; longitudinally opposed, laterally extending end edges 56; and a system of elastomeric gathering members, such as a system including leg elastics 60 and waist elastics 62. The longitudinal side edges 54 define leg openings 58 for the diaper 20, and optionally, are curvilinear and contoured. The lateral end edges 56 are illustrated as straight, but optionally, may be curvilinear. The diaper 20 may also include additional components to assist in the acquisition, distribution and storage of bodily exudates. For example, the diaper 20 may include a transport layer, such as described in U.S. Pat. No. 4,798,603, to Meyer et al., or a surge management layer, such as described in European Patent Office Publication No. 0539703, published May 5, 1993.

With regard to the designated surfaces of the absorbent article and its components, the various upper or bodyside surfaces are configured to face toward the body of the wearer when the absorbent article is worn by the wearer for ordinary use. The various opposing or lower surfaces are configured to face away from the wearer's body when the absorbent article is worn by the wearer.

The diaper 20 generally defines a longitudinally extending length dimension 64, and a laterally extending width dimension 66, as representatively illustrated in FIG. 1. The diaper may have any desired shape, such as rectangular, I-shaped, a generally hourglass shape, or a T-shape.

The outer cover 48 and the liner 30 may be generally coextensive (e.g., FIG. 1), or optionally, may be non-coextensive. Either or both of the outer cover 48 and the liner 30 may have length and width dimensions which are generally larger than those of the absorbent structure 50 and extend beyond the corresponding dimensions of the absorbent structure 50 to provide longitudinal side edges 54 and lateral end edges 56 which may be connected or otherwise associated together in an operable manner. As used herein when describing the liner 30 in relation to the outer cover 48 and vice versa, the term "associated" encompasses configurations in which the liner 30 is directly joined to the outer cover 48, and configurations where the liner 30 is indirectly joined to the outer cover 48 by affixing portions of the liner 30 to intermediate members which in turn are affixed to at least portions of the outer cover 48. The liner 30 and the outer cover 48 can, for example, be joined to each other in at least a portion of the diaper periphery 52 by attachment mechanisms (not shown) such as adhesive bonds, sonic bonds, thermal bonds, pinning, stitching, or a variety of other attachment techniques known in the art, as well as combinations thereof.

Various woven and nonwoven fabrics may be used for the liner 30. For example, the liner 30 may be composed of a meltblown or spunbonded web of polyolefin fibers. The liner 30 may also be a bonded-carded web composed of natural and/or synthetic fibers. The liner 30 may be composed of a substantially hydrophobic material, and the hydrophobic material may, optionally, be treated with a surfactant, or otherwise processed, to impart a desired level of wettability and hydrophilicity. Specifically, the liner 30 may be a nonwoven, spunbond, polypropylene fabric composed of about 2.8 to about 3.2 denier fibers formed into a web having a basis weight of about 22 gsm and a density of about 0.06 g/cc.

The liner 30 may also be surface treated with about 0.3 weight percent of a surfactant mixture that contains a mixture of AHCOVEL Base N-62 surfactant and GLUCOPON 220UP surfactant in about a 3:1 ratio based on a total weight of the surfactant mixture. The AHCOVEL Base N-62 surfactant is purchased from Hodgson Textile Chemicals Inc., a business having offices in Mount Holly, N.C., and includes a blend of hydrogenated ethoxylated castor oil and sorbitan monooleate in a 55:45 weight ratio. The GLUCOPON 220UP surfactant is purchased from Henkel Corporation, Gulph Mills, Pa., and includes alkyl polyglycoside. The surfactant may also include additional ingredients such as aloe. The surfactant may be applied by any conventional means, such as spraying, printing, brush coating, foam or the like. The surfactant may be applied to the entire liner 30 or may be selectively applied to particular sections of the liner 30, such as the medial section along the longitudinal centerline of a diaper, to provide greater wettability of such sections.

The outer cover 48 may suitably be composed of a material which is either liquid permeable or liquid impermeable. It is generally desirable that the outer cover 48 be formed from a material which is substantially liquid impermeable. For example, a typical outer cover 48 can be manufactured from a thin plastic film or other flexible liquid impermeable material. For example, the outer cover 48 may be formed from a polyethylene film having a thickness of from about 0.012 mm (0.5 mil) to about 0.051 mm (2.0 mils). If desirous of presenting the outer cover 48 with a more cloth-like feel, the outer cover 48 may include a polyethylene film having laminated to the lower or outer surface thereof a nonwoven web, such as a spunbond web of polyolefin fibers. For example, a polyethylene film having a thickness of about 0.015 mm (0.6 mil) may have thermally laminated thereto a spunbond web of polyolefin fibers, which fibers have a thickness of about 1.5 to about 2.5 denier per filament, which nonwoven web has a basis weight of about 24 gsm (0.7 osy). Methods of forming such cloth-like outer covers are known to those skilled in the art.

Further, the outer cover 48 may be formed of a woven or nonwoven fibrous web layer which has been totally or partially constructed or treated to impart a desired level of liquid impermeability to selected regions that are adjacent or proximate the absorbent structure 50. Still further, the outer cover 48 may optionally be composed of micro-porous "breathable" material which permits vapors to escape from the absorbent structure 50 while still preventing liquid exudates from passing through the outer cover 48.

The absorbent structure 50 may include a matrix of hydrophilic fibers, such as a web of cellulosic fluff, mixed with particles of a high-absorbency material commonly known as superabsorbent material. In a particular version, the absorbent structure 50 includes a mixture of superabsorbent hydrogel-forming particles and wood pulp fluff. The wood pulp fluff may be exchanged with synthetic polymeric, meltblown fibers or with a combination of meltblown fibers and natural fibers. The superabsorbent particles may be substantially homogeneously mixed with the hydrophilic fibers or may be non-uniformly mixed. One suitable type of wood pulp fluff is identified with the trade designation CR-1654, available from Bowater, Inc., Greenville, S.C., and is a bleached, highly absorbent sulfate wood pulp containing primarily soft wood fibers. A special densification pulp, identified with the trade designation ND-416, available from Weyerhaeuser of Federal Way, Wash., is also suitable for use.

To limit any undesired movement of superabsorbent material, the disposable diaper 20 may also include a wrap sheet (not shown) which is placed immediately adjacent and partially or totally around the entire absorbent structure 50, around an individual layer of the absorbent structure 50, or around one or more selected elements of the absorbent structure 50, as desired. The wrap sheet is typically a layer of absorbent material which covers at least the upper and lower surfaces of the absorbent structure 50 prior to the absorbent structure 50 being situated between the outer cover 48 and the liner 30.

The absorbent structure 50 may have any of a number of shapes. For example, the absorbent structure 50 may be rectangular, I-shaped or T-shaped. It is generally desired that the absorbent structure 50 be narrower in the crotch portion than the rear or front portion(s).

The diaper 20 has been discussed in detail herein. However, it will be understood by those skilled in the art that the foregoing description also applies to a training pant and to an adult incontinence pant or garment, whether formed as a pant or provided as a refastenable garment.

Turning now to folding configurations or "footprints", a disposable absorbent article, that is, for purposes of illustration only and not by way of limitation, the diaper 20 illustrated in FIG. 1, is folded to provide a reduced or more compact configuration or footprint. The various compact footprints, created by different folding techniques, are compared to the unfolded footprint, that is, the measurement of the area as defined immediately within the outer perimeter or diaper periphery 52. Each folded compact configuration of each absorbent article, namely, the diaper 20 described below and shown in FIGS. 3-8 is measured along a longitudinal direction or length dimension 138 (generally along a "y" direction) and a lateral direction or width dimension 140 (generally along an "x" direction).

In addition, a depth dimension 142 (generally along a "z" direction, generally positioned perpendicular relative to a plane formed by the "x" and "y" directions), is measured in both the unfolded footprint of the diaper/diaper pant 20, and the folded compact footprint.

Figure 2:
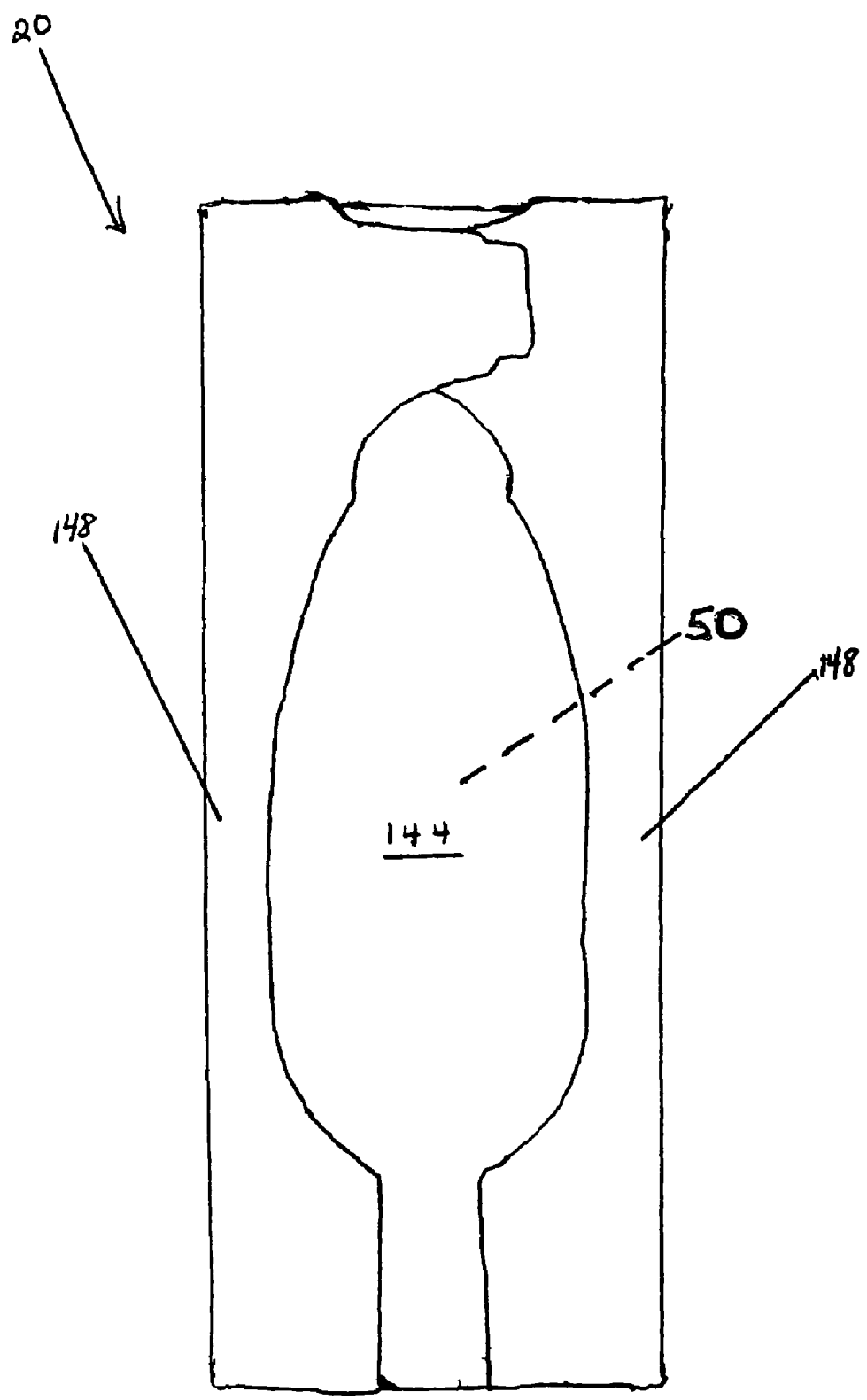
FIG. 2 illustrates a perspective view of the absorbent article in which each side is folded over the center.
Figure 3A:
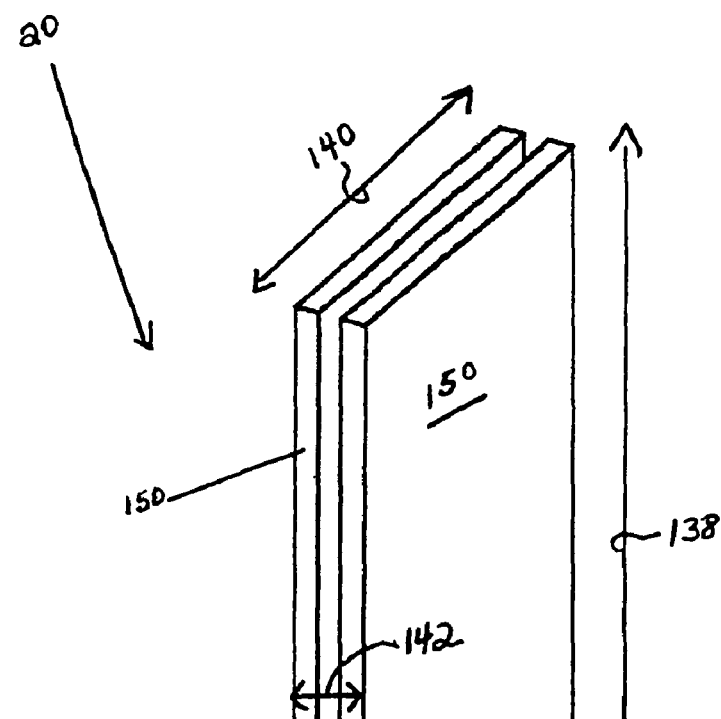
FIG. 3A illustrates a perspective view of the absorbent article of FIG. 2 folded into a bifolded configuration.

In initially folding a disposable absorbent article such as, by way of non-limiting example, a diaper 20, each side 148 is folded inward over the area containing the absorbent structure 50, as shown in FIG. 2. The diaper 20 is then folded again at approximately the center 144 to provide a bifolded diaper 20 having two overlapping panels 150 of approximately equal length, as schematically illustrated in FIG. 3A. A pre-fastened diaper or disposable swim pant achieves this bifolded configuration by folding the front ear portions and the back ear portions, as shown in FIG. 3B.

Figure 4:
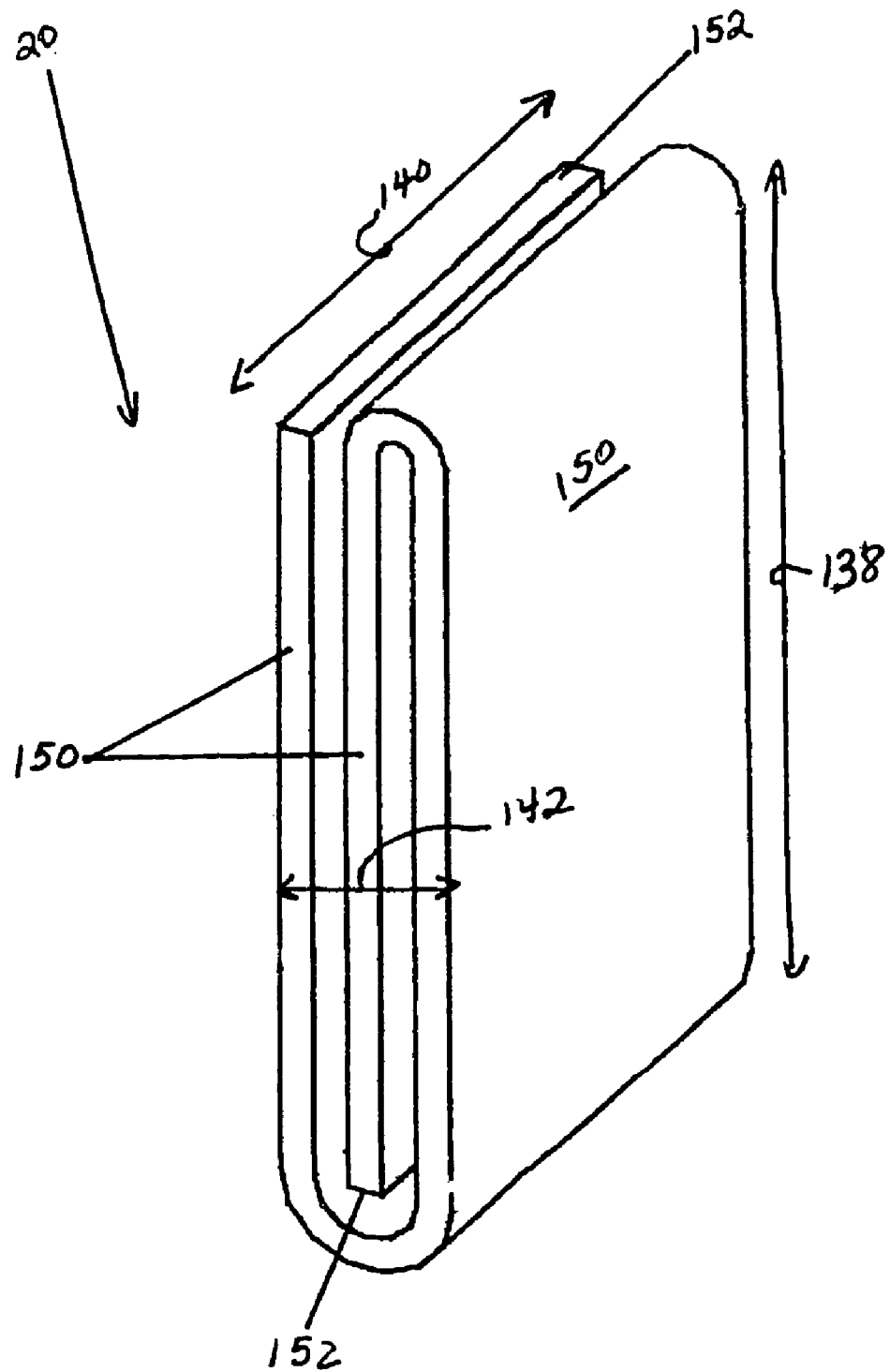
FIG. 4 illustrates a perspective view of the absorbent article of FIG. 2 folded into a trifolded configuration.

In an alternative, as schematically illustrated in FIG. 4, the diaper 20, folded initially as shown in FIG. 2 is folded such that each end 152 is folded over and overlaps about a third of the other to provide three approximately equal and overlapping panels 150. In this manner, a trifolded diaper 20 is provided.

Figure 3B:
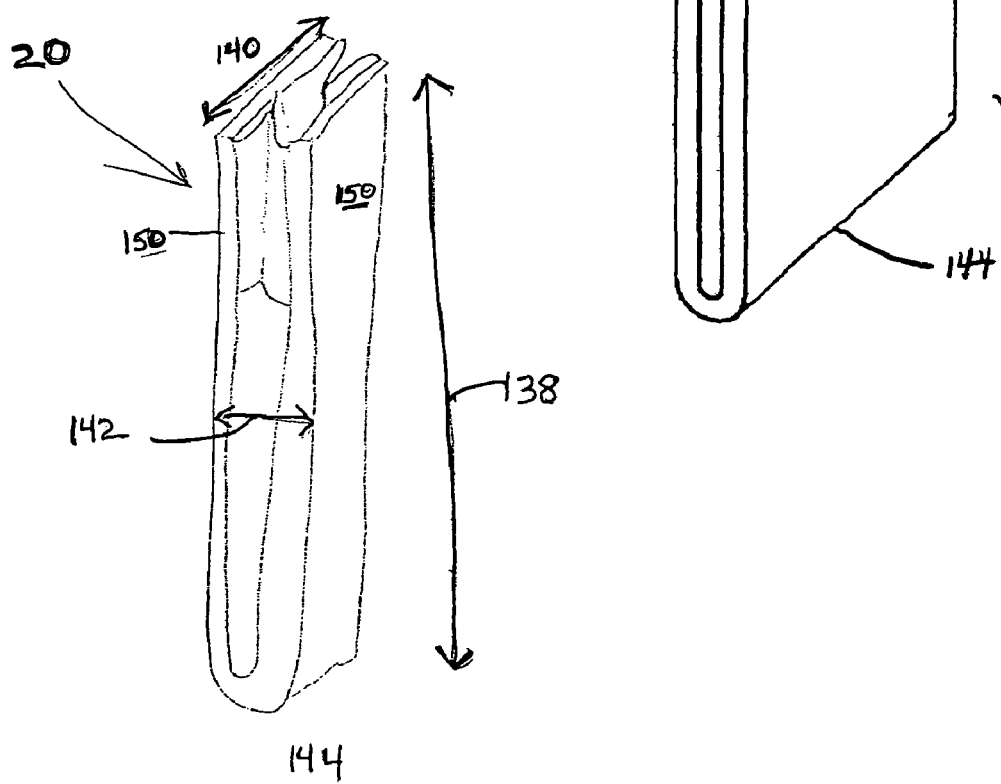
FIG. 3B illustrates a perspective view of a prefastened absorbent article folded into a bifolded configuration.
Figure 5:
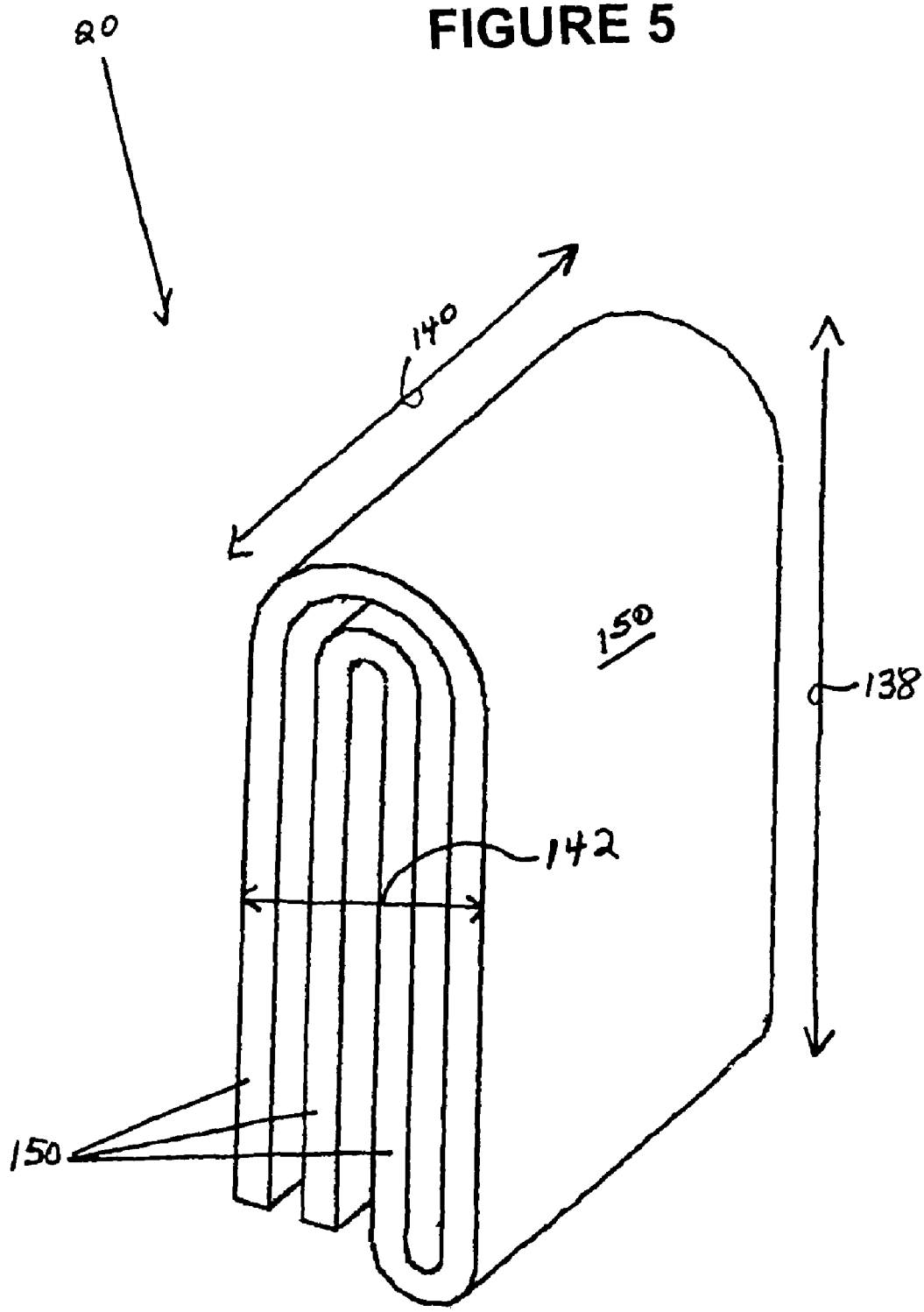
FIG. 5 illustrates a perspective view of the absorbent article of FIG. 3A or 3B folded into a quadrifolded configuration.

In another alternative, as schematically illustrated in FIG. 5, the bifolded diaper 20 shown in FIG. 3A or 3B is then overlapped again to provide a quadrifolded diaper pant 20 having four approximately equal and overlapping panels 150.

Figure 6:
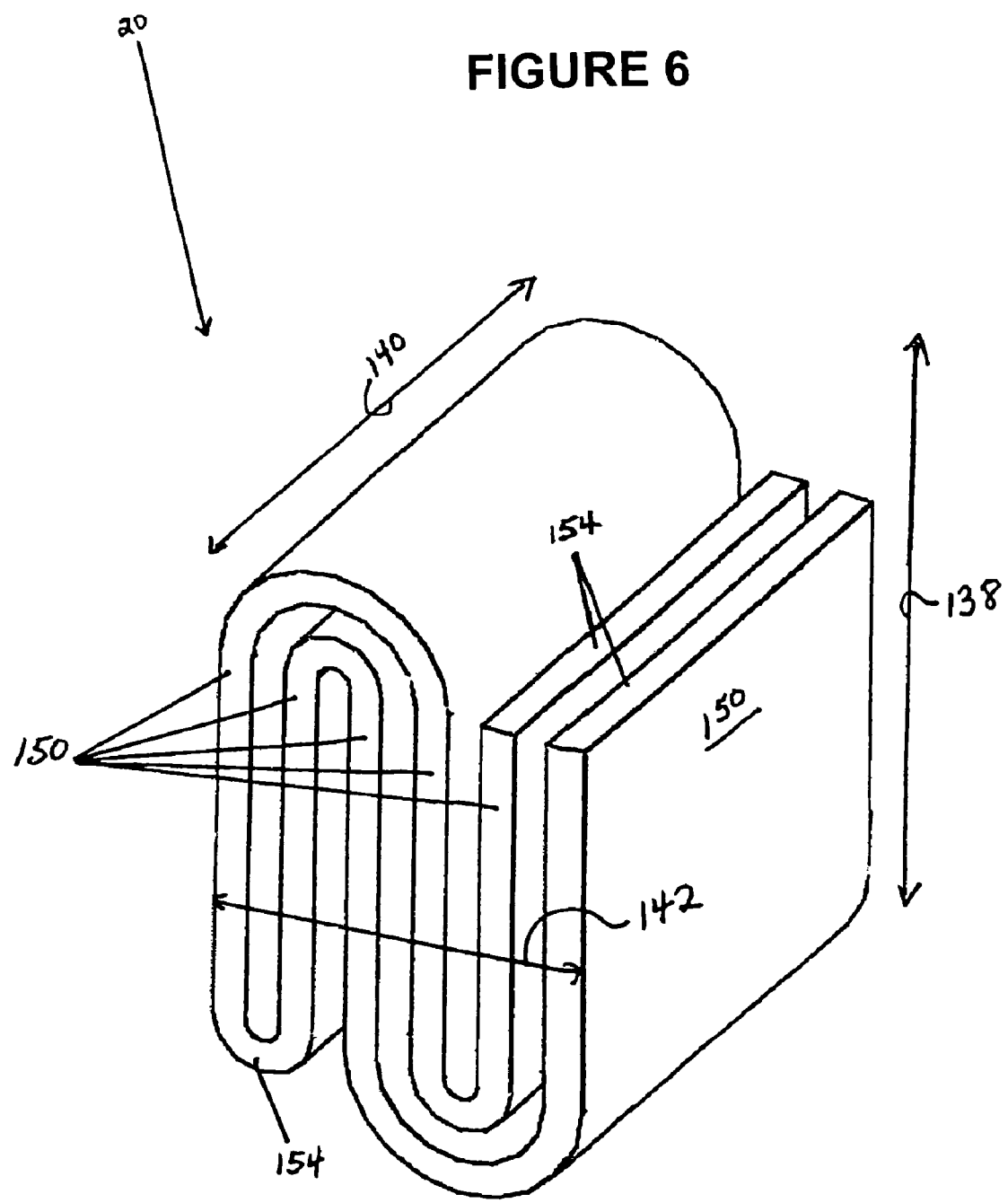
FIG. 6 illustrates a perspective view of the absorbent article of FIG. 3A or 3B having each ended folded over a center to provide generally an "S" configuration.

In yet another alternative, as schematically illustrated in FIG. 6, the bifolded diaper 20 shown in FIG. 3A or 3B is then folded such that approximately one third of each bifolded end 154 of the folded diaper is folded over each side of a center portion to provide an "S" folded diaper having six approximately equal and overlapping panels 150.

Figure 7:
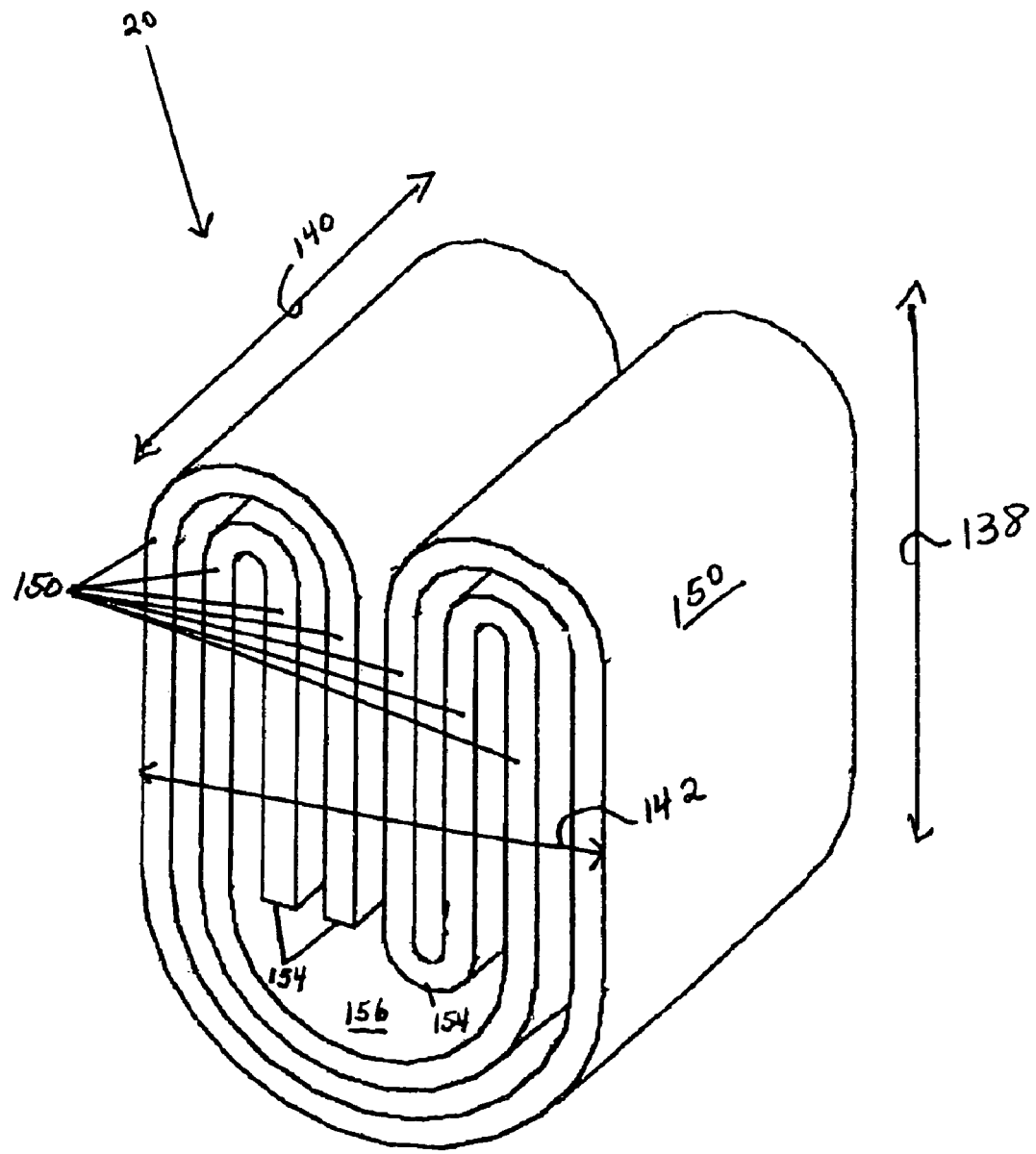
FIG. 7 illustrates a perspective view of the absorbent article of FIG. 3A or 3B which has each end folded inward to provide generally a "Pretzel;" configuration.

In still yet another alternative, as schematically illustrated in FIG. 7, each end 154 of the bifolded diaper 20 shown in FIG. 3A or 3B is overlapped inwardly, toward a center portion 156 to provide a "Pretzel" fold having eight overlapping panels 150.

Figure 8:
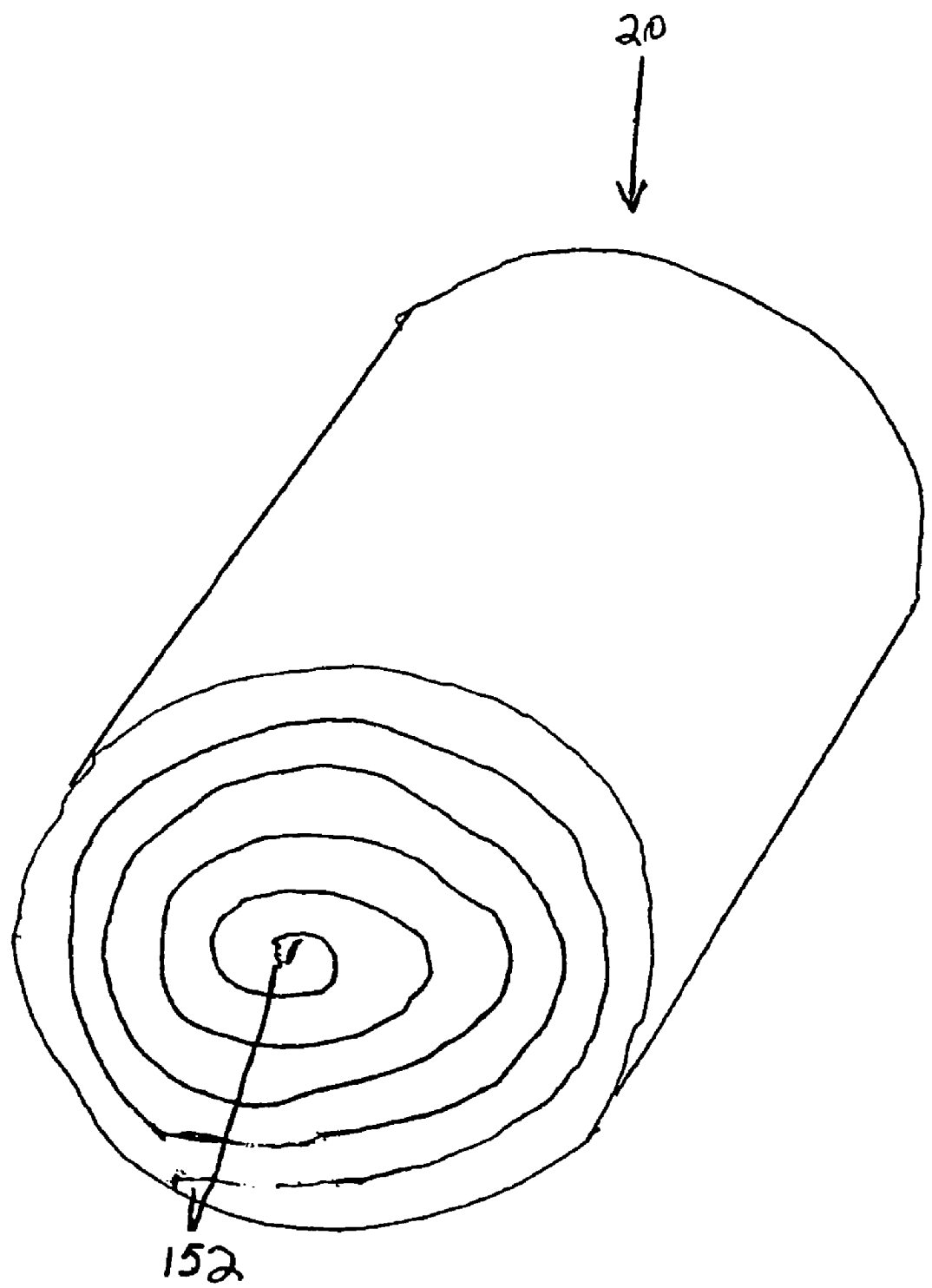
FIG. 8 illustrates a perspective view of the absorbent article of FIG. 2 which has been rolled into a generally cylindrical configuration.

In still a further version, as illustrated in FIG. 8, the diaper 20 of FIG. 2 is rolled from one end to the other to form a generally cylindrical shape. This configuration, providing a continuous rotation of the diaper 20 around a center, differs from folds; it has no planar surface in the folded configuration, other than each end, since it forms, generally, a cylindrical shape. It will be understood, however, that the present article may be folded in any manner consistent with the present invention, and the foregoing folding techniques and rolled technique are not intended to limit the scope of the invention.

In folding the article, folding the fasteners is usually taken into consideration. Fasteners desirably are not folded in the width (cross-machine) direction, because such folding often impacts the ability of the fasteners to fasten to the landing zone attachment panel. Damage to the fasteners may occur if the fastener is bent such that a portion of the fastener lies in one plane while another portion lies in a curve and/or another plane. Specifically, the fasteners may be damaged such that they are not capable of maintaining a sufficient contact with the attachment panel, thereby causing the article to unfasten from a torso. Therefore, the fasteners are desirably maintained in a consistent plane or planar surface when folded with the article in any of the foregoing folded configurations.

The article may be folded by hand or by machine folded (not shown). The article is then packaged.

Figure 9:
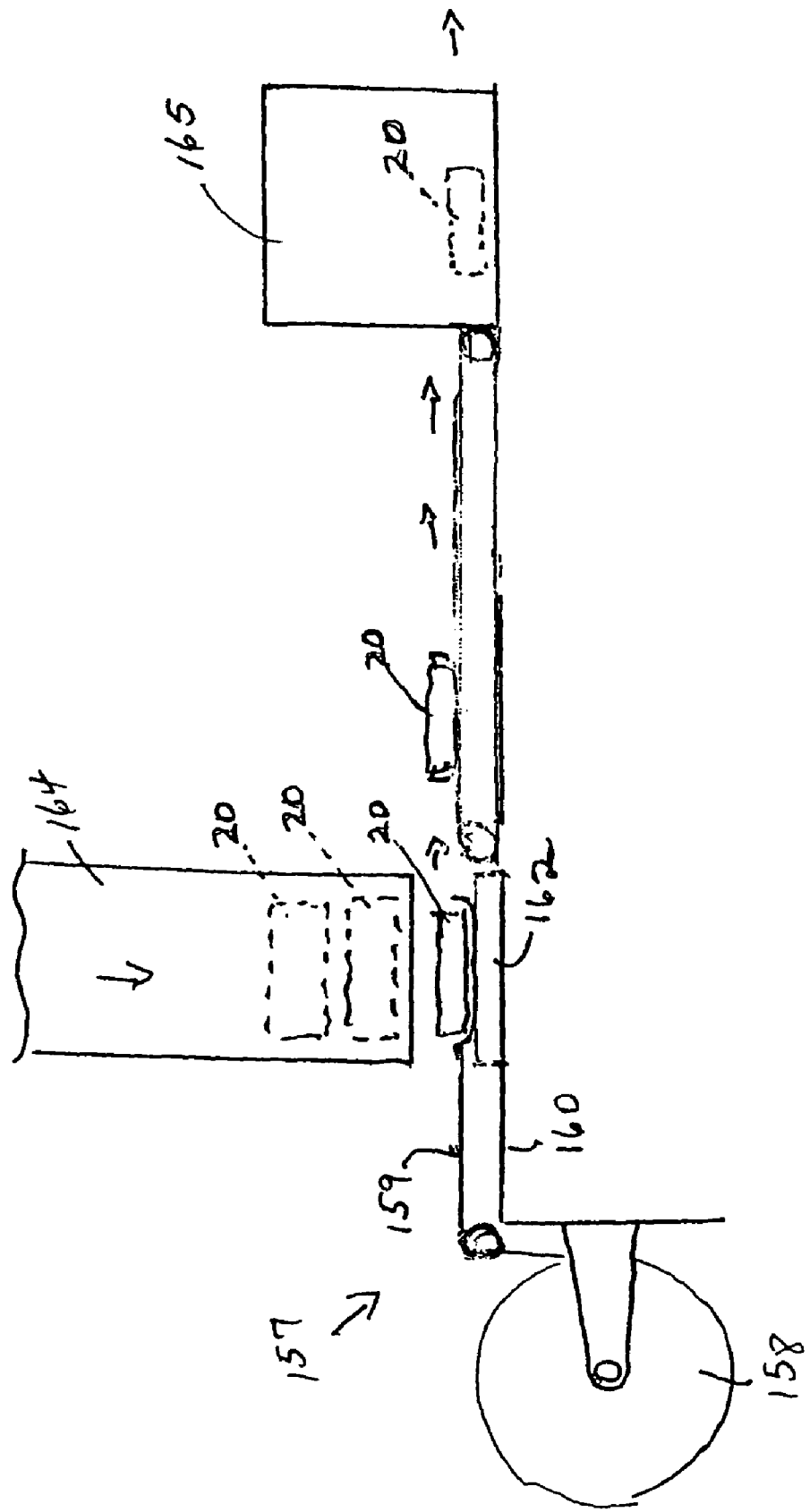
FIG. 9 illustrates a schematic representation of an apparatus for packaging disposable absorbent articles.

Schematically illustrated shown in FIG. 9 is one method and apparatus 157 of packaging a diaper 20. In this example, a first reel 158 has sheet material 159 which is rotatably supported on a bed 160 having a vacuum cavity former 162 provided where the diaper 20 is disposed. Diapers 20, such as, for example, the diaper 20 folded as illustrated in FIG. 6, are provided at a loading station 164 and they are disposed on the sheet material 159 over the cavity former 162. The diapers 20 are carried to a packaging station 165 which has a vacuum chamber (not shown). The packaging station 165 also contains film (not shown) and a sealing apparatus (not shown) for sealing the diapers 20 in the cavities while they are in the vacuum chamber. The diapers 20 in the forming cavities 162 are carried into the packaging station 165 and the chamber is closed. A vacuum is applied to the diapers 20 and the cavities 162, and film is then positioned and sealed over each cavity via sealing devices, such as thermal sealing, ultrasonic bonding, or any other sealing methods known by those skilled in the art. The vacuum depressurizes the chamber in the packaging station to a pressure which is less than the atmospheric pressure outside of the chamber. After the package is sealed, the vacuum is removed from the chamber, and the chamber and the articles sealed in packages therein are permitted to return to regular atmospheric pressure, which results in compression of the articles in the packages, providing a soft package (form-fill-seal) which is formed about the diaper 20. The packaged article 190 may thereafter be removed (not shown). Any type of packaging device may be utilized which permits the diaper 20 to be situated in the packaging described herein. Many techniques and apparatus for vacuum packaging are known in the art and commercially available.

The amount of vacuum is typically an amount necessary to result in compression of the article so that it may be contained and reduced in size within and along with the package. The amount of vacuum suitable for use in packages of the present invention is generally no more than 32; alternatively, no more than 31; alternatively, no more than 30; alternatively, no more than 29; alternatively, no more than 28; alternatively, no more than 27; alternatively, no more than 26; alternatively, no more than 25; alternatively, no more than 20; alternatively, no more than 15; alternatively, no more than 14; alternatively, no more than 13; alternatively, no more than 12; alternatively, no more than 11; alternatively, no more than 10; alternatively, no more than 9; alternatively, no more than 8; alternatively, no more than 7; and finally, alternatively, no more than 6 inches of Mercury. The amount of vacuum suitable for use in packages of the present invention is generally no less than 5; alternatively, no less than 6; alternatively, no less than 7; alternatively, no less than 8; alternatively, no less than 9; alternatively, no less than 10; alternatively, no less than 11; alternatively, no less than 12; alternatively, no less than 13; alternatively, no less than 14; alternatively, no less than 15; alternatively, no less than 17; alternatively, no less than 23; alternatively, no less than 25; alternatively, no less than 26; alternatively, no less than 27; alternatively, no less than 28; alternatively, no less than 29; alternatively, no less than 30; and finally, alternatively, no less than 31 inches of Mercury. Thus, the amount of vacuum may be no less than 5 up to no more than 32 inches of Mercury; although the approximate amount of vacuum may vary according to, inter alia, the general design and intended use of the package.

In the version of FIG. 9, the package is at least partially a preformed package. The compression or pressure on the article may be exerted at least partially by the package. Alternatively, the package may be formed around the diaper 20.

The article, desirably vacuum packaged, is sealed in a package desirably constructed of a material with a substantially low gas permeability, including, but not limited to, a polymeric film, such as, by way of non-limiting example, a polyethylene terephthalate (PET), a polyvinyldichloride (PVDC), having an oxygen transmission of about less than 3.0 cc/100 in$^2$/24 hours at 73 degrees F. and 0 percent relative humidity (RH). Multilayer films, each providing a different function, may be utilized. For example, one layer may have a heat sealable property, such as polypropylene or polyethylene, another layer may provide strength, such as polyester and/or nylon, and another layer may provide substantially reduced gas permeability, such as PET or PVDC. Also, films with reduced permeability to vapors (that is, films that have substantially low gas permeability or are substantially gas impermeable for a variety of applications) can themselves be composites, such as where one layer is a flexible polymer, such as polyurethane, polyethylene, ether polyurethane, or polypropylene, while another layer is coated on or coextruded and serves as a barrier layer. Barrier layers can generally be viewed as substantially organic based or substantially inorganic based. For example, U.S. Pat. No. 3,442,686 describes a film composite in which silicon oxide coatings are deposited on polymers to serve as a barrier layer. This produces barrier coatings on even quite thin polymer films of oxygen transmission rate properties of about 0.2 cc/100 in$^2$/day and similar water vapor transmission rate properties. However, it will be appreciated that a variety of materials having substantially low gas permeability or substantially gas impermeable material(s) known in the art may be used.

Desirably, with a substantially low gas permeable material and/or package, the gas permeability rate is less than about 5.0 cc/100 in$^2$/24 hours to about 0.05 cc/100 in$^2$/24 hours. More desirably, the gas permeability rate is less than 4.0 cc/100 in$^2$/24 hours to about 0.07 cc/100 in$^2$/24 hours. Even more desirably, the gas permeability rate is less than about 3.0 cc/100 in$^2$/24 hours to about 0.10 cc/100 in$^2$/24 hours. Even more desirably, the gas permeability rate is less than about 2.0 cc/100 in$^2$/24 hours to about 0.10 cc/100 in$^2$/24 hours.

In addition, it is advantageous to control heat during folding and packaging the article. The temperature of at least the absorbent core is desirably kept below about 110 degrees C. Even more desirably, the temperature of at least the absorbent core is kept at below about 80 degrees C. Yet even more desirably, the temperature of at least the absorbent core is kept below about 50 degrees C. Still even more desirably, the temperature of at least the absorbent core should be kept below about 24 degrees C.

Schematically illustrated in FIGS. 10A and 10B is a second method and apparatus 103 of packaging a diaper 20. In this example, a web W of packaging material is fed from a feed roll (not shown) to a rotary cutter (not shown) by means, including a pair of draw rolls 134. The web W may be a polymeric film, as mentioned above.

The apparatus 103 wraps and seals the flat web around the diaper 20. The web W is guided in such a manner that longitudinal edge portions 114 of the web W are brought into close proximity to form, at F, a fin seal seam as the web is drawn forward by the rolls 134. The fin seal may be formed at F with many methods known in the art, by way of example, ultrasonic, heat, adhesive, or as shown in the apparatus 103, a blast of hot air is introduced through nozzle 107. The hot air may melt the polymeric film so that the adjacent surfaces of the edge portions 114 become tacky, where after the surfaces are sealed together by passage of the fin seal F through the nip of a pair of rollers 110 thereby forming the seam.

The web W is drawn by the rolls 134 over an idler roller 120 and along a horizontal forming plate 115. Top conveyor 106 and bottom conveyor 105 transport folded diapers 20 from a folding process (not shown) and place the folded diaper 20 on the web W as the web W is being folded around the diaper 20. The speed of the conveyors 105, 106 relative to the speed of the web W can be varied to position the diapers 20 closer or further apart. Additionally, the diapers 20 on the conveyors 105, 106 may be spaced with a uniform distance between diapers 20, or the diapers may be spaced such that the spacing varies between diapers 20. Rollers 116 and guides 117 form the web around the diapers 20 against the plate 115 with the edge portions 114 vertical and held open by a predetermined amount by guides 118 and 119. The nozzle 107 has a flattened end 107 and is positioned in the open fin seal F and hot air is directed against the adjacent surfaces of the edge portions 114 through a multiplicity of holes in the flattened end 107$a$ of the nozzle. The rollers 110 are geared together by gears 111 and loaded against each other by a spring 111$a$. The fin seal is drawn through the nip of the rollers 110 by the draw rolls 134 and the rollers 110 are thus caused to rotate and press together the longitudinal edge portions 114 to make the seam and at the same time to cool the seam prior to the fin seal being folded flat by a guide 113.

The surface of the rollers 110 which contact the longitudinal edge portions 114 may be smooth. Alternatively the surface of the rollers which contact the longitudinal edge portions 114 may be textured to change the quality or aesthetics of the fin seal F. Additionally, the rollers 110 may be driven by drive 112. Additionally, the rollers 110 may have a cutting device to trim the fin seal, or an additional trimming device may be inserted between rollers 110 and guide 113.

The rolls 134 may be made of a flexible material which allows the rolls 134 to deform and thus maintain contact with the web W at all times, when the diaper 20 is between the rolls 134 as well as when only the web W is present between the rolls 134. Alternatively the rolls 134 may be mounted such that when a diaper passes between the rolls, a constant force is maintained but the rolls 134 travel away from one another, and come back to one another when the diaper 20 is no longer between the rolls 134.

The web W containing the diapers 20 with a completed fin seal then passes through sealer 135 which has sealing regions 135A and 135B. Sealing region 135A on the top roll of the sealer 135 may be matched with a mating sealing region 135A on the bottom roll of the sealer 135. Corresponding sealing region 135B on the top roll of the sealer 135 may be matched with a mating sealing region 135B on the bottom roll of the sealer 135. The sealer 135 is thus able to produce a first end seal formed by sealing region 135A, and a second end seal formed by sealing region 135B, where the first end seal differs from the second end seal. Representative sealing regions 135A and 135B are illustrated in FIG. 13C. The sealing regions 135A and 135B are shown with a seal producing region 133 and a cutting region 136. The seal producing region 133 may be of many patterns as known in the art. The cutting region 136 of sealing region 135B is an example of a nested opening tab which may be used in particular embodiments of the invention. The cutting region 136 as show is integrated into the sealer 135; alternatively the cutting region 136 may be located on a separate set of rollers, before or after the sealer 135. The sealer 135 may product the seal using heat, pressure, ultrasonic energy, or any other method known in the art, or a combination of two or more methods.

A disposable absorbent article, such as a diaper as described above, a training pant, or an adult incontinence pant or garment, may be packaged individually in a package with a feature to provide for easy opening. This singly packaged disposable absorbent article provides the end-user with a portable, convenient, and discrete method for using disposable absorbent products. Absorbent articles may be packaged individually in packages including one, two, or more pieces of packaging material. These packages may contain an absorbent article that is in an unfolded configuration or the article may be folded as described above, or in another suitable manner, to provide a smaller more discreet package.

The present invention presents the user with an opening element that provides a location to grasp the package facilitating opening. This opening element may be provided on numerous configurations of packages, as discussed in the following non-limiting examples. Desirably these opening elements provide the user with a mechanism to open the package at a seal with a controlled opening. This controlled opening, may allow the user to create an opening in the package for removal of the disposable absorbent article, without separating the package into two unconnected pieces.

Figure 11A:
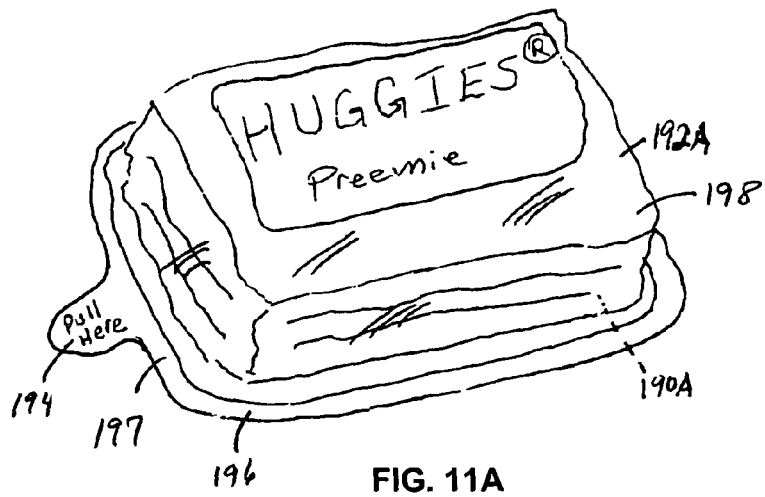
FIGS. 11A-11C illustrate different versions of packages in which disposable absorbent articles may be packaged.
Figure 11B:
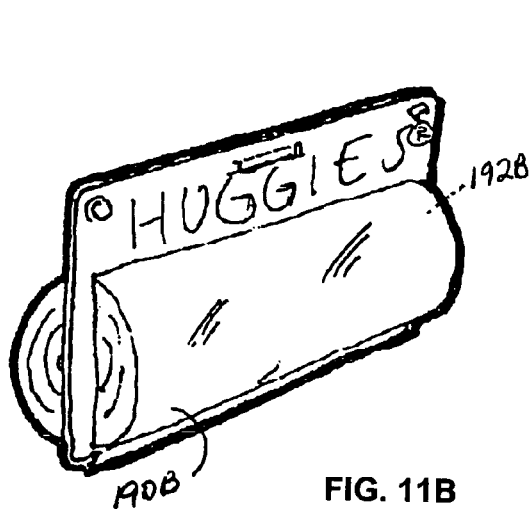
Figure 11C:
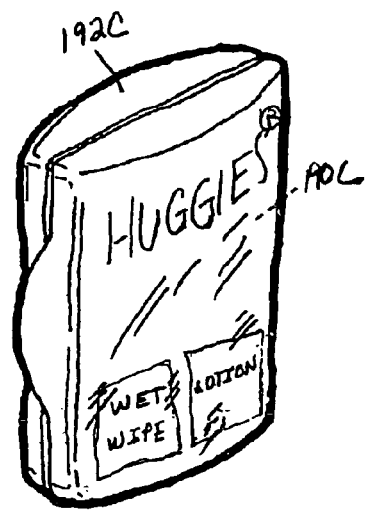

There are numerous different package configurations that may include the present invention. FIGS. 11A-11C illustrate several different packaged absorbent articles 190. Package 192A illustrates a form-fill-seal package holding an absorbent article 190A (such as, for example, the article shown in FIG. 6), as also generally shown in FIG. 9. Package 192B, as shown by FIG. 11B, shows a blister package having a living hinge and holding an absorbent article 190B (such as the article shown in FIG. 8). FIG. 11C illustrates an injection molded package having a living hinge (not shown) which holds a absorbent article 190C. The packages 190A-190C desirably include curvilinear corners, and each desirably provides size information (FIG. 11A) for the absorbent article contained therein, as well as one or more attractive decorations, such as one or more letters, numbers, symbols, designs and/or patterns, an area to write a user's name and other information, and so forth. In addition, a wet sheet packet, a lotion pocket, a changing sheet, a disposal bag, one or more coupons, and so forth may be included on an inside of the package, as illustrated in 190C, or on an outside of the package (not shown). Desirably, each package 190A-190C will open without any small pieces of the package tearing away separately, which is undesirable in the presence of small children and infants. The packages may be provided such that a plurality of singly packaged articles are releasably coupled together by, for example, but not by way of limitation, perforations, bands, adhesives, and so forth.

Further desirably, as illustrated in FIG. 11A, the package 192A will have an opening element. For example the package 192A, as illustrated has a pull tab 194. The pull tab 194 desirably extends beyond a seal 196 of the package 192A, so that it is easy to grasp between a thumb and a finger by a caregiver, and permits easy opening of the package while maintaining the package 192 in one piece after being opened, and after the article has been removed. The package is opened by grasping the pull tab 194 and pulling relative to the package. Alternatively, instead of a pull tab, the opening element may be an opening tab. A package with an opening tab is opened by grasping one portion of the opening tab and pulling relative to a second portion of the opening tab, thereby allowing the enclosed article to be removed. An opening element may be an extension of the packaging material that extends beyond a seal that forms the package.

The pull tab 194 shown in FIG. 11A may be formed as a portion of the top material 197 of the package 192A, and is desirably, but not by way of limitation, not coterminous with the bottom material 198 of the package 192A to which the top material 192 is sealed. The pull tab 194 may have pull indicia such as words, symbols, and so forth (for example, but not by way of limitation, "Pull Here" illustrated in FIG. 11A). The pull tab 194 may be formed of a thicker material, or may be embossed or otherwise textured, and so forth, to provide easy grasping and pulling by a caregiver. The pull tab 194 may be formed in one or more corners of the package 192A, or one or more pull tabs 194 may be provided on any portion(s) of the package 192A (not shown). Desirably, the edges of the pull tab 194 are curvilinear.

FIGS. 12A, 12B, 12C, 13A, 13B, 14A, 14B illustrate several different packages which may contain a single absorbent article. Each of these figures illustrates different configurations of a singly packaged absorbent article which, by way of non-limiting example, include the present invention.

Package 80 as represented in FIG. 12A illustrates a fin seal package containing a folded absorbent article 81A (not directly shown) (such as, for example, the article shown in FIG. 6). Package 80 has end seals 86, a fin seal 90, two folds 83, and an opening tab 88. The end seals 86 may be any seal as known in the art, for example, adhesive, thermal, pressure, cohesive, ultrasonic, or any combination of these. The fin seal 90 may also be a variety of seals as known in the art.

As used herein when describing a first portion of packaging material in relationship to a second portion of packaging material, the term "operatively associated" encompasses configurations in which the first portion of package material is directly joined to the second portion of packaging material, and configurations where the first portion of packaging material is indirectly joined to the second portion of packaging material by affixing the first portion of packaging material to intermediate members which in turn are affixed the second portion of packaging material. The first portion of packaging material and the second portion of packaging material may, for example, be joined to each other such as adhesive bonds, sonic bonds, thermal bonds, pinning, stitching, or a variety of other attachment techniques known in the art, as well as combinations thereof. The first portion of packaging material and the second portion of packaging material may be, before operative association, located on separate discrete pieces of material. Alternatively, the first portion of packaging material and the second portion of packaging material may be, before operative association, located on the same piece of packaging material.

Package 80 as represented in FIG. 12A, may be formed using the apparatus illustrated in FIG. 10 or any other similar apparatus as know in the art. The end seal 86 may be continuous across the width of the package as illustrated in FIG. 12A. Alternatively, the end seal 86 may not be continuous across the width of the package. The end seal 86 may be formed such that it has a pattern to make opening easier, or the pattern may provide information about the product which is contained in the package. The end seal 86 may be formed in a multi step process, 1) an end seal 86 is created that is not continuous but contains the articles within the package, 2) the package from step 1 is exposed to a vacuum, 3) the end seal 86 is completed, forming an air tight package and 4) the vacuum is removed delivering a vacuum packed article.

FIG. 12B shows a cross section of the package 80 of FIG. 12A as viewed along the line X-X'. FIG. 12B shows absorbent article 81A, and fin seal 90. For illustrative purposes only, fin seal 90 as shown in FIG. 12B is substantially perpendicular to the surface of the package 80. Alternatively, the fin seal 90 may be folded to be substantially parallel and laying on the surface of the package 80, or the fin seal 90 may be in some position between substantially perpendicular and substantially parallel to the surface of the package 80.

FIG. 12C is similar to FIG. 12B but illustrates an alternative to the fin seal 90. The package illustrated in FIG. 12C has an overlap seal 92. The overlap seal may be a variety of seals as know in the art, as described above. A package with an overlap seal 92 may be formed using an apparatus similar to that illustrated in FIG. 10, but with appropriate modifications to the fin sealing portion as known in the art. Specifically modification including removal may be desired of rollers 116, guides 118, 119, rollers 110, drive 112 and gears 111.

Package 80' as illustrated in FIG. 13A illustrates a three-sided seal package containing a folded absorbent article 81B (such as, for example, the article illustrated in FIG. 6). Package 80' has end seals 86, a side seal 94, a fold 83, and an opening tab 88. The end seals 86 and the side seal 94 may be any seal as known in the art, as described above. The end seals 86 and the side seal 94 may be made in the same step in the packaging process and end seals 86 and side seal 94 may be the same seal (e.g. both adhesive seals). Alternatively the end seals 86 may be made in a first step and the side seal 94 may be made in a second step in the packaging process. In this situation, the end seals 86 may be a different seal than the side seal 94 (e.g. end seal 86 an adhesive, side seal 94 ultrasonic seal). The side seal 94 as illustrated in FIG. 13A extends the length of the opening tab 88. Alternatively the side seal 94 may extend a portion of the length of the opening tab 88, or the side seal 94 may not extend into the opening tab 88 and may terminate at the end seal 86.

FIG. 13B illustrates a cross section of the package 80' of FIG. 13A as viewed along the line X-X'. FIG. 13B illustrates absorbent article 81B, a side seal 94, and a fold 83.

Package 80" as represented in FIG. 14A illustrates a four sided seal package containing a folded absorbent article 81C (such as, for example, the article shown in FIG. 6). Package 80" has end seals 86, two side seals 94, and an opening tab 88. The end seals 86 and the side seals 94 may be any seal as known in the art, as described above. The end seals 86 and the side seals 94 may be made in the same step in the packaging process and end seals 86 and side seals 94 may be the same seal (e.g. both adhesive seals). Alternatively the end seals 86 may be made in a first step and the side seals 94 may be made in a second step in the packaging process. In this situation, the end seals 86 may be a different seal than the side seal 94 (e.g. end seal 86 an adhesive, side seal 94 ultrasonic seal). Alternatively three for the four seals may be formed in one step, and the fourth seal may be formed in a second step. The side seal 94 as shown in FIG. 14A extends the length of the opening tab 88. Alternatively the side seal 94 may extend a portion of the length of the opening tab 88, or the side seal 94 may not extend into the opening tab 88 and may terminate at the end seal 86.

FIG. 14B illustrates a cross section of the package 80" of FIG. 14A as viewed along the line X-X'. FIG. 14B illustrates absorbent article 81C and two side seals 94. Package 80", as illustrated in FIGS. 14A and 14B, is formed from first piece of packaging material and a second piece of packaging material. The first piece of packaging material and the second piece of packaging material may be the same material; alternatively the first piece of packaging material may be different from the second piece of packaging material.

Packages 80, 80' and 80" illustrated in FIGS. 12A, 13A and 14A may be made from many different materials. The material forming the package may be clear to allow the user to see the article in the packages. The material may have some indicia to indicate the size, or type of product enclosed in the package. This indicia may include color, or texture. Additionally the material may be printed with the type, the size or information relating to the usage of the product enclosed in the package.

FIG. 15 illustrates two packages formed with a common piece of packaging material and separated, wherein the two packages have then been placed next to one another with the first package's opening tab edge adjacent to the second package's opening tab edge. For illustrative purposes only, the two packages are each similar to fin seal package 80A as may be formed using the apparatus shown in FIG. 10A. Alternatively, the consecutive packages may be any two packages that are formed with at least one common piece of packaging material, which may be but are not limited to fin seal packages, overlap seal packages, three-sided seal packages, and four sided-seal packages.

In FIG. 15, the packages 80 are illustrated with end seals 86, and opening tabs 88. The opening tabs 88 have been configured with a pattern wherein the shape of one opening tab 88 is substantially nested with the shape of at least one immediately adjacent opening tab 88. The nesting of the opening tabs 88 is desirable to reduce the amount of waste that is generated from the originally supplied web of packaging material. Additionally, the nesting of the opening tabs 88 may eliminate the need to remove waste material during packaging, and in this way may simplify the packaging process.

Figure 16A:
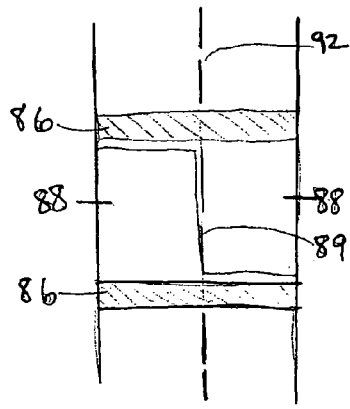
FIGS. 16A-16E illustrate various nested opening elements.
Figure 16B:
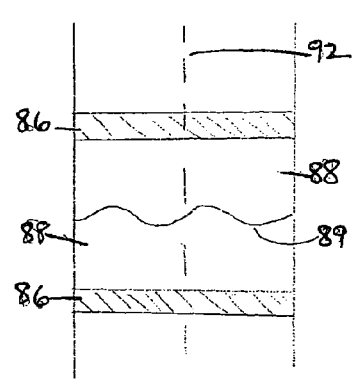
Figure 16C:
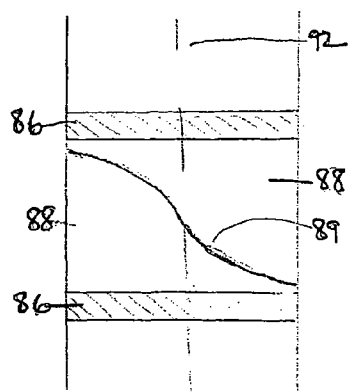
Figure 16D:
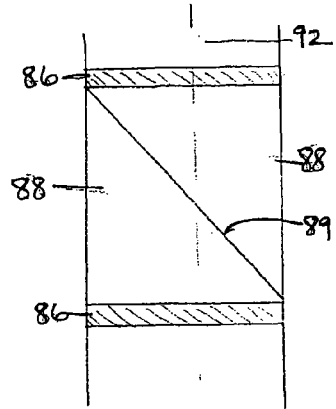
Figure 16E:
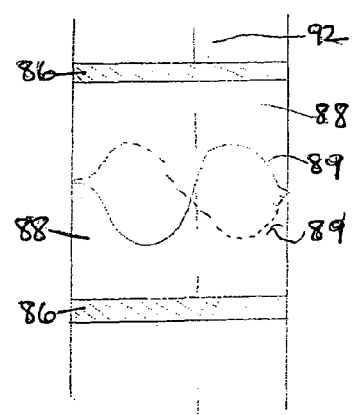

FIGS. 16A-16E illustrate the opening tab region of two packages with various nested opening tabs 88, wherein the two packages have been separated, and then have been placed next to one another with the first package's opening tab edge 89 adjacent to the second package's opening tab edge 89. For illustrative purposes only, the packages in FIG. 16A-16E are overlap seal packages. An opening tab 88 is formed from a first portion 88' and a second portion 88" (as illustrated in FIGS. 16A and 16E). As illustrated in FIG. 16A, the first portion 88', shown on the front of the package, may be directly in front of and coterminous with the second portion 88" shown on the back of the package. Alternatively, as illustrated in FIG. 16E, the first portion 88', shown on the front of the package, may be offset from, and non-coterminous with the second portion 88", shown on the back of the package. As described above, a package may be opened by grasping the first portion 88' and pulling relative to the second portion 88", separating the first portion 88' and the second portion 88", thereby allowing the enclosed article to be removed.

For an opening tab 88 to be functional, the length of each portion, which is the maximum distance that the packaging material that forms the opening tab 88 extends from the end seal 86, is desirably at least about 6 mm. If the maximum distance that the packaging material extends from the end seal 86 is less than about 6 mm, it becomes difficult for the user to grasp the opening tab 88 with their fingers and to open the package. The first portion 88' and the second portion 88" of the opening tab 88 may be operatively associated or may be formed from a single piece of material. In the example of a fin sealed package, the first portion 88', located on the front of the package, and the second portion 88", located on the back of the package, may be formed from the same piece of material, separated by the fold 83. In a three or four sided seal package the first portion 88' (not shown) and the second portion 88" (not shown) may be operatively associated by a side seal.

The opening tab 88 length may be at least 6; alternatively, at least 7; alternatively, at least 8; alternatively, at least 9; alternatively, at least 10; alternatively, at least 11; alternatively, at least 12; alternatively, at least 13; alternatively, at least 14; alternatively, at least 15; alternatively, at least 16; alternatively, at least 17; alternatively, at least 18; alternatively, at least 19; alternatively, at least 20; alternatively, at least 21; alternatively, at least 22; alternatively, at least 23; alternatively, at least 24; alternatively, at least 25; or finally, alternatively, at least 26 millimeters. In addition, the opening tab 88 length may be less than 27; alternatively, less than 26; alternatively, less than 25; alternatively, less than 24; alternatively, less than 23; alternatively, less than 22; alternatively, less than 21; alternatively, less than 20; alternatively, less than 19; alternatively, less than 18; alternatively, less than 17; alternatively, less than 16; alternatively, less than 15; alternatively, less than 14; alternatively, less than 13; alternatively, less than 12; alternatively, less than 11; alternatively, less than 10; alternatively, less than 9; alternatively, less than 8; or finally, alternatively, less than 7 millimeters. Thus, the amount of tab length may be at least 6 up to less than 27 millimeters; although the approximate tab length may vary according to, inter alia, the general design and intended use of the package.

FIG. 16A illustrates the opening tab region of two packages with nested opening tabs 88, end seals 86, overlap seal 92, and opening tab edge 89. The opening tab edge 89 is substantially linear with substantially right angles. The opening tab edge 89 may be formed using the apparatus of FIG. 10A, therefore the first portion and the second portion of the opening tab 88 are conterminous, meaning the first portion and the second portion of the opening tab 88 have opening tab edges 89 that substantially overlap.

FIGS. 16B, 16C and 16D show opening tab regions of two packages with alternative opening tab edges 89. In each, FIGS. 16B, 16C, and 16D, the opening tab edge 89 may be formed using the apparatus of FIG. 10A, therefore the first and second portions of the opening tabs 88 are conterminous.

FIG. 16E shows the opening tab region of two packages with nested opening tabs 88 where the tab edges 89 are substantially non-coterminous. The material making up the package may have been perforated, or in some other way the tab edge 89 may have been preformed but not separated before the package was formed. The tab edge 89 may have been formed in a process prior to the packaging process or as a part of the packaging process before the package was formed. FIG. 16E shows the opening tabs 88, end seals 86, overlap seal 92, and opening tab edge 89 and 89'. Opening tab edge 89 is present on the packaging material on the front of the packages. Opening tab edge 89' is present on the packaging material on the back of the packages. Part of the first portion and part of the second portion of the opening tab 88 are therefore visible when the package is viewed from the front.

Figure 17A:
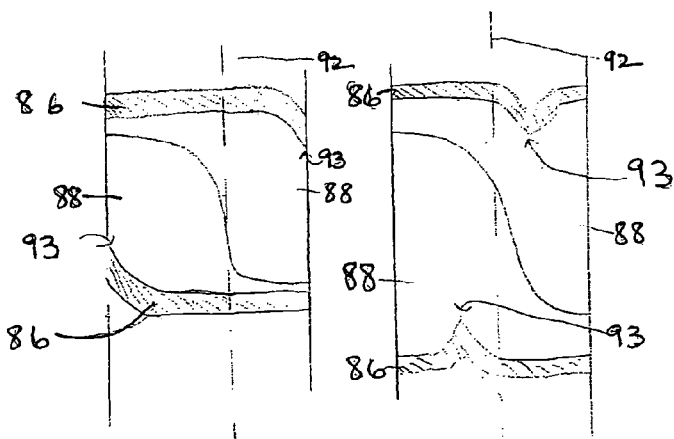
FIGS. 17A-17C illustrate various tear initiating end seals.
Figure 17B:
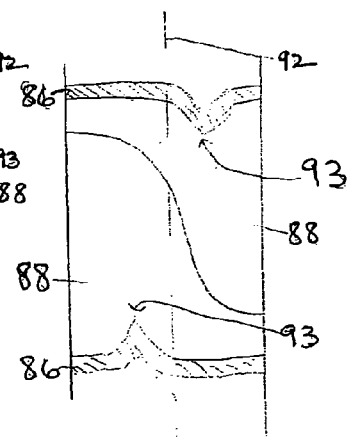
Figure 17C:
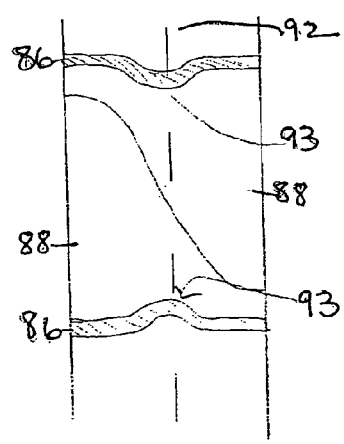

FIGS. 17A-17C illustrates the opening tab region of two packages with various tear initiating end seals, again, where the two packages have been separated, and then have been placed next to one another with the first package's opening tab edge 89 adjacent to the second package's opening tab edge 89. FIG. 17A illustrates overlap seal 92, end seals 86, opening tabs 88, and tear initiating area 93. In contrast to the end seals 86 shown in FIGS. 16A-16E, the end seal 86 in FIG. 17A has a tear initiating area 93 that protrudes into the opening tab 88. When the first and second portions of the opening tab 88 are separated, this protrusion is the first area of the end seal 86 that begins to be separated and therefore open. This tear initiating area 93 provides a starting point for the end seal 86 to open, therefore the force required to open the end seal 86 may be less then the forces to open an end seal without a tear initiating area 93. The tear initiating area 93 in FIG. 17A comes to a point at the edge of the package. Alternatively, as illustrated in FIG. 17B, the tear initiating area 93 may come to a point at some location between the two edges of the package. Alternatively, as illustrated in FIG. 17C, the tear initiating area may be curved at some location between the two edges of the package, or at the edge of the package (not shown).

Figure 18A:
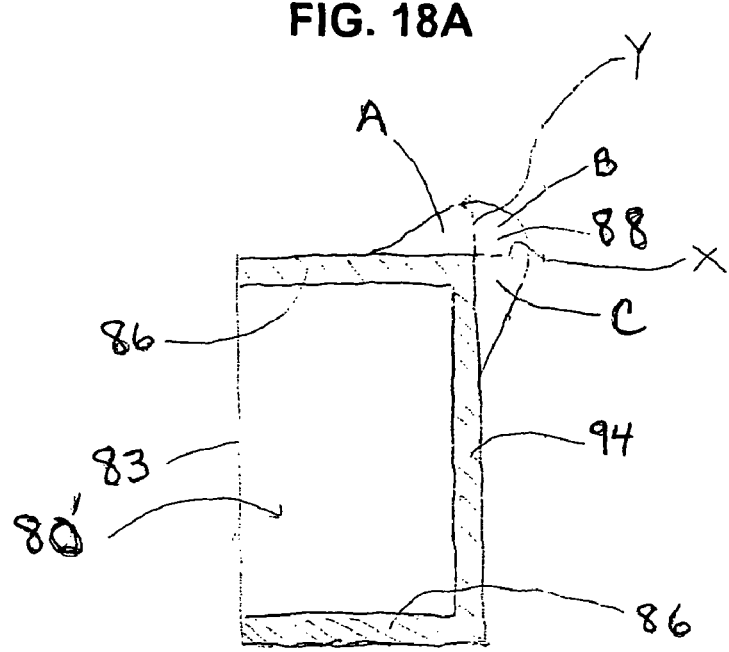
FIGS. 18A-18B illustrate three-sided seal packages with opening elements.

FIG. 18A representatively illustrates a three-sided seal package 80' with the fold 83 forming a longitudinal edge of the package. The package 80' has end seals 86, side seam 94, and opening tab 88. The opening tab 88 of the package 80' illustrated in FIG. 18A extends longitudinally outward from the end seal 86, and laterally outward from the side seam 94. The opening tab 88 in this orientation provides two benefits.

First, the opening tab 88 provides the user with a mechanism with which to open the product. Second, when many packages 80' are together in a stack or row, the opening tab 88 will protrude from both the lateral side, and the longitudinal side, providing a method to easily remove a single product from the stack or row from both the lateral and longitudinal side.

The area of the opening tab 88 that extends laterally beyond the lateral seam is determined in the following manner (as illustrated in FIG. 18A). First the area of the opening tab 88 is determined by measurement with a ruler, or with an alternative appropriate method as known in the art. Second, a line X is drawn along the exterior edge of the end seam 86 extending onto the opening tab 88. Next the area of the opening tab 88 which is on the opposite side of the line X from the product. The opening tab 88 with area A, area B, and area C, shown in FIG. 18A would have a total area of A+B+C, and an area of opening tab 88 extending from a lateral side of A+B. The percentage of the opening tab 88 extending from the lateral seam would be 100*[(A+B)/(A+B+C)].

Utilizing the same method to determine the area of the opening tab 88 extending from a longitudinal seam would result in area B+C, and the percentage of the opening tab 88 extending from the longitudinal seam would be 100*[(B+C)/(A+B+C)].

The opening tab 88 may not extend from a longitudinal seam, alternatively the opening tab 88 may extend from a longitudinal seam at least 5; alternatively, at least 10; alternatively, at least 14; alternatively, at least 20; alternatively, at least 23; alternatively, at least 30; alternatively, at least 33; alternatively, at least 40; alternatively, at least 46; alternatively, at least 49; alternatively, at least 53; alternatively, at least 61; alternatively, at least 67; alternatively, at least 70; alternatively, at least 74; alternatively, at least 78; alternatively, at least 81; alternatively, at least 86; alternatively, at least 90; alternatively, at least 91; alternatively, at least 94; or finally, alternatively, at least 97 percent. In addition, the opening tab 88 may extend from a longitudinal seam 100 percent; alternatively the opening tab 88 may extent for a longitudinal seam no more than 97; alternatively, no more than 91; alternatively, no more than 88; alternatively, no more than 82; alternatively, no more than 75; alternatively, no more than 68; alternatively, no more than 63; alternatively, no more than 58; alternatively, no more than 53; alternatively, no more than 49; alternatively, no more than 44; alternatively, no more than 40; alternatively, no more than 36; alternatively, no more than 31; alternatively, no more than 26; alternatively, no more than 21; alternatively, no more than 15; alternatively, no more than 12; alternatively, no more than 10; alternatively, no more than 8; or finally, alternatively, no more than 5 percent. Thus, the amount of the opening tab 88 may extend from a longitudinal seam may vary from 0 percent up to 100 percent; although the approximate amount of extension may vary according to, inter alia, the general design and intended use of the package.

The opening tab 88 may not extend from a lateral seam, alternatively the opening tab 88 may extend from a lateral seam at least 5; alternatively, at least 10; alternatively, at least 14; alternatively, at least 20; alternatively, at least 23; alternatively, at least 30; alternatively, at least 33; alternatively, at least 40; alternatively, at least 46; alternatively, at least 49; alternatively, at least 53; alternatively, at least 61; alternatively, at least 67; alternatively, at least 70; alternatively, at least 74; alternatively, at least 78; alternatively, at least 81; alternatively, at least 86; alternatively, at least 90; alternatively, at least 91; alternatively, at least 94; or finally, alternatively, at least 97 percent. In addition, the opening tab 88 may extend from a lateral seam 100 percent; alternatively the opening tab 88 may extent for a lateral seam no more than 97;

alternatively, no more than 91; alternatively, no more than 88; alternatively, no more than 82; alternatively, no more than 75; alternatively, no more than 68; alternatively, no more than 63; alternatively, no more than 58; alternatively, no more than 53; alternatively, no more than 49; alternatively, no more than 44; alternatively, no more than 40; alternatively, no more than 36; alternatively, no more than 31; alternatively, no more than 26; alternatively, no more than 21; alternatively, no more than 15; alternatively, no more than 12; alternatively, no more than 10; alternatively, no more than 8; or finally, alternatively, no more than 5 percent. Thus, the amount of the opening tab 88 may extend from a lateral seam may vary from 0 percent up to 100 percent; although the approximate amount of extension may vary according to, inter alia, the general design and intended use of the package.

Figure 18B:
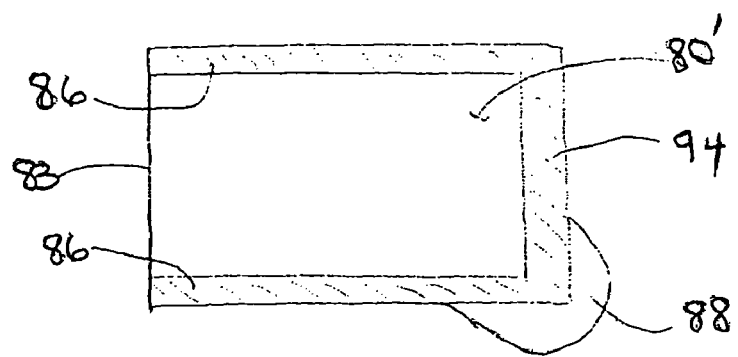

FIG. 18B representatively illustrates a three-sided sealed package 80' with the fold 83 forming a lateral edge of the package. The package 80' has end seals 86, side seal 94, and opening tab 88. The opening tab 88 of the package 80' shown in FIG. 18B extends longitudinally outward from the side seal 94, and laterally outward from the end seam 86.

The singly packaged absorbent article is intended to provide benefits including convenience due to portability, as well as discretion. In order to provide these benefits, it is desired that the absorbent article, when packaged, will have a configuration that permits it to be placed in a purse, a jacket pocket, a pants pocket, or a shirt pocket. Each type of pocket has somewhat different dimensions, but generally, it is desirable to have an article, for example, a single packaged diaper, which has a width dimension of less than 153 mm, a length dimension of less than 280 mm, and a depth dimension of less than 45 mm. More desirably, the article will have a width dimension 138 of less than 127 mm, a length dimension 140 of less than 140 mm, and a depth dimension of less than 38 mm. Even more desirably, the article will have a width dimension of less than 117 mm, a length dimension of less than 102 mm, and a depth dimension of less than 45 mm. Yet even more desirably, the article will have a width dimension of less than 117 mm, a length dimension of less than 97 mm, and a depth dimension of less than 34 mm. Such ranges described herein provide a footprint, that is, an area, or projected area, as well as a volume for the packaged absorbent article so that it easily fits into a shirt pocket, a pants pocket, a jacket pocket, a small purse, and so forth, to provide ease in carrying and concealing the article.

The area or footprint of the folded absorbent article is compared to the area of the unfolded article as measured when the article is laid flat with unretracted elastics and extended to ungathered length configuration of the article (as exemplified by the disposable diaper 20). Desirably, the ratio between the area of the folded configuration and the unfolded configuration is less than 0.14. More desirably, the ratio between the folded configuration and the unfolded configuration is less than 0.13. Even more desirably, the ratio between the folded configuration and the unfolded configuration is less than 0.12. Yet even more desirably, the ratio between the folded configuration and the unfolded configuration is less than 0.11. However, yet even more desirably, the ratio between the folded configuration and the unfolded configuration is less than 0.10. Still yet even more desirably, the ratio between the folded configuration and the unfolded configuration is less than 0.09. Still yet even more desirably, the ratio between the folded configuration and the unfolded configuration is less than 0.07. Yet even more desirably, the ratio between the folded configuration and the unfolded configuration is less than 0.05.

When an article is packaged, that is by way of non-limiting example vacuum packaged, it is expected that its size will be reduced in width, length, and depth, i.e., in three dimensions. Thus the size of the article is first reduced through the folding process and then further reduced through the packaging process. As measured in two dimensions, width and length (area—$cm^2$) and compared against a substantially similarly folded un-packaged article, the article is desirably reduced in area by more than about 10 percent. Even more desirably, the article is reduced in area by more than about 12 percent. Yet even more desirably, the article is reduced in area by more than about 15 percent. Still yet even more desirably, the article is reduced in area by more than about 17 percent. However, even more desirably, the article is reduced in area by more than about 20 percent. Yet even more desirably, the article is reduced in volume by more than about 22 percent.

In addition to the area of the folded absorbent article, the volume of the article is desired to be such that it provides portability. The volume of the folded and singly packaged absorbent article is desirably less than 500 $cm^3$. More desirably, the volume of the absorbent article is less than 250 $cm^3$. Even more desirably, the volume of the absorbent article is less than 200 $cm^3$. Yet even more desirably, the volume of the absorbent article is less than 165 $cm^3$. Still yet even more desirably, the volume of the absorbent article is less than 115 $cm^3$. However, yet even more desirably, the volume of the absorbent article is less than 82 $cm^3$.

When the article, as described above is packaged and measured in three dimensions i.e., width, length and depth (volume—$cm^3$) and compared against a substantially similarly folded un-packaged article, the article is desirably reduced in volume by more than about 10 percent. Even more desirably, the article is reduced in volume by more than about 15 percent. Yet even more desirably, the article is reduced in volume by more than about 20 percent. Still yet even more desirably, the article is reduced in volume by more than about 30 percent. However, even more desirably, the article is reduced in area by more than about 40 percent. Yet even more desirably, the article is reduced in volume by more than about 45 percent.

In addition to the importance of the size of the package to provide the stated benefits, the invention provides an improved means for opening the singly packaged disposable absorbent article. The amount of force required to open the package may be influenced by the relative rigidities of the materials being separated. The relative force of opening is less when the rigidities of the materials being separated are different from one another, as compared to the force of opening when the rigidities of the materials being separated are the same. Material rigidity may be modified in a number of ways to provide desired packaging and opening characteristics. For example, one way to modify the rigidity of packaging materials includes changing the composition of the compounds that make up the material. A second way to modify the rigidity of packaging materials is to change the thickness of the material. A third way to modify the rigidity of packaging materials is by changing the topography of the materials, for instance by embossing. These modifications, as well as other modifications as known in the art may be used to either increase or decrease the rigidity of the packaging materials. Alternatively, these and other modifications as known in the art may be used in combination to modify the rigidity of the packaging materials.

A suitable technique for determining the rigidity, stiffness values described herein is a Gurley Stiffness test, a description of which is set forth in TAPPI Standard Test T 543 pm-84 (Stiffness of paper (Gurley type stiffness tester)). A suitable testing apparatus is a Gurley Digital Stiffness Tester: Model 4171-0 manufactured by Teledyne Gurley (514 Fulton Street, Troy, N.Y. 12181-0088). This instrument allows the testing of a wide variety of materials through the use of various lengths and widths in combination with the use of a 5, 25, 50, or 200 gram weight placed in one of three positions on the pointer of the apparatus.

It will be appreciated that details of the packages of the invention, given for purposes of illustration, are not to be construed as limiting the scope of this invention. Although only a few exemplary aspects of this invention have been described in detail above, those skilled in the art will readily appreciate that many modifications are possible in the exemplary aspects without materially departing from the novel teachings and advantages of this invention. Accordingly, all such modifications are intended to be included within the scope of this invention, which is defined in the following claims and all equivalents thereto. Further, it is recognized that many aspects may be conceived that do not achieve all of the advantages of some aspects, particularly of the preferred aspects, yet the absence of a particular advantage should not be construed to necessarily mean that such an aspect is outside the scope of the present invention.

What is claimed is:

1. A package enclosing a single disposable garment-type absorbent article, the package comprising a first piece of material and a second piece of material, the first piece of material and the second piece of material being operatively associated with one another to enclose the absorbent article, the operative association defining a seal, wherein the first piece of material and the second piece of material have different rigidities, and wherein at least a portion of the first piece of material and at least a portion of the second piece of material extend beyond the seal to deliver an opening element.

2. The package of claim 1, wherein the first piece of material is more rigid than the second piece of material.

3. The package of claim 1, wherein the second piece of material is more rigid than the first piece of material.

4. The package of claim 1, wherein the seal defines at least one lateral edge and at least one longitudinal edge, wherein a portion of the opening element extends beyond at least one lateral edge of the seal, and a portion of the opening element extends beyond at least one longitudinal edge of the seal.

5. The package of claim 4, wherein at least 50% of the opening element extends beyond at least one lateral edge of the seal, and at least 50% of the opening element extends beyond at least one longitudinal edge of the seal.

6. The package of claim 1, wherein the portion of the first piece of material and the portion of the second piece of material are non-coterminous.

7. The package of claim 1, wherein the package is vacuum packed.

8. The package of claim 1, wherein the opening element is coded to indicate the size or type of the absorbent article.

9. The package of claim 1, wherein the absorbent article has a ratio in a folded configuration to an unfolded configuration of no more than 0.09.

10. A package enclosing a single disposable garment-type absorbent article, the package comprising a layer of material having an interior surface and an exterior surface, the layer of material configured to provide an interior space and at least two lateral seals, the absorbent article being situated within the interior space of the package, wherein a portion of the layer of material extends beyond at least one lateral seal to provide an opening element comprising an upper portion and a lower portion having different rigidities, wherein the absorbent article has a folded configuration and an unfolded configuration, and wherein the absorbent article has a ratio of the folded configuration to the unfolded configuration of less than 0.14.

11. The package of claim 10 further comprising a longitudinal seal.

12. The package of claim 10 wherein a portion of the layer of material is operatively associated with another portion of the layer of material to provide the interior space.

13. The package of clam 10 wherein the upper portion and the lower portion are non-coterminous.

14. The package of claim 10, wherein the absorbent article is vacuum packaged.

15. The package of claim 10, wherein the opening element is coded to indicate the size or type of the absorbent article.

16. The package of claim 15, wherein the opening element is color coded to indicate the size or type of the absorbent article.

17. The package of claim 15, wherein the opening element is tactilely coded to indicate the size or type of the absorbent article.

18. A package enclosing a single disposable garment-type absorbent article, the package comprising a first piece of material and a second piece of material, the first piece of material and the second piece of material being operatively associated with one another to enclose the absorbent article, the operative association defining a seal, wherein the first piece of material and the second piece of material have different rigidities wherein the seal defines at least one lateral edge and at least one longitudinal edge, wherein at least a portion of the first piece of material and at least a portion of the second piece of material extend beyond the seal to deliver an opening tab, wherein a portion of the opening tab extends beyond at least one lateral edge of the seal, and a portion of the opening tab extends beyond at least one longitudinal edge of the seal.

19. The package of claim 18, wherein the first piece of material is more rigid than the second piece of material.

20. The package of claim 18, wherein the second piece of material is more rigid than the first piece of material.

21. The package of claim 18, wherein the package is vacuum packed.

22. The package of claim 18, wherein the absorbent article has a ratio in the folded configuration to the unfolded configuration of no more than 0.09.

* * * * *